US008614365B2

(12) United States Patent
Hammons et al.

(10) Patent No.: US 8,614,365 B2
(45) Date of Patent: Dec. 24, 2013

(54) ABSORBENT ARTICLE

(75) Inventors: John Lee Hammons, Hamilton, OH (US); Sybille Fuchs, Frankfurt am Main (DE); Jody Lynn Hoying, Mainville, OH (US); Timothy Ian Mullane, Union, KY (US); Casandre Maffett Walsh, Cincinnati, OH (US); Donna Marie Caudill, Madeira, OH (US); Naomi Ruth Nelson, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 824 days.

(21) Appl. No.: 11/881,115

(22) Filed: Jul. 25, 2007

(65) Prior Publication Data

US 2009/0030390 A1    Jan. 29, 2009

(51) Int. Cl.
*A61F 13/15* (2006.01)

(52) U.S. Cl.
USPC ........................................................ 604/383

(58) Field of Classification Search
USPC ........................................................ 604/383
See application file for complete search history.

(56) References Cited

U.S. PATENT DOCUMENTS

| 4,747,991 | A | 5/1988 | Bishop et al. |
| 5,968,029 | A | 10/1999 | Chappell et al. |
| 5,998,696 | A | 12/1999 | Schone |
| 6,452,064 | B1 | 9/2002 | Thoren et al. |
| 6,498,284 | B1 | 12/2002 | Roe |
| 6,911,574 | B1 | 6/2005 | Mizutani |
| 6,965,058 | B1 | 11/2005 | Raidel et al. |
| 7,005,558 | B1 | 2/2006 | Johansson et al. |
| 7,060,867 | B2 | 6/2006 | Jameson |
| 7,067,711 | B2 | 6/2006 | Kuroda et al. |
| 2003/0078553 | A1 | 4/2003 | Wada et al. |
| 2003/0114811 | A1 | 6/2003 | Christon et al. |
| 2003/0125687 | A1 | 7/2003 | Gubernick et al. |
| 2003/0214083 | A1 | 11/2003 | Kelly et al. |
| 2004/0122386 | A1 | 6/2004 | Mocadlo |

(Continued)

FOREIGN PATENT DOCUMENTS

| EP | 0 934 737 A1 | 8/1999 |
| JP | 05269168 | 10/1993 |
| JP | 2005278885 A | 10/2005 |
| WO | WO-2006/009996 | 1/2006 |

OTHER PUBLICATIONS

PCT International Search Report dated Nov. 17, 2008.

(Continued)

*Primary Examiner* — Lynne Anderson
(74) *Attorney, Agent, or Firm* — Andrew J. Hagerty

(57) ABSTRACT

An absorbent article having a topsheet having a first portion and a second portion. The topsheet has a longitudinal centerline and a transverse centerline. The topsheet has an area. The second portion can differ in structure from the first portion. The second portion can have a structurally modified zone. The structurally modified zone has a periphery, a length, and a long axis. The length is the maximum straight-line dimension between two points on the periphery. The long axis extends between two points on the periphery separated by the length. The long axis of the structurally modified zone can be asymmetric to the longitudinal centerline. The structurally modified zone can make up more than about 5% of the area of the topsheet. The topsheet can have a lotion zone, the long axis of which is asymmetric to the longitudinal centerline and the transverse centerline.

12 Claims, 21 Drawing Sheets

(56) References Cited

U.S. PATENT DOCUMENTS

| | | |
|---|---|---|
| 2004/0176734 A1 | 9/2004 | Rasmussen et al. |
| 2005/0059942 A1 | 3/2005 | Krautkramer et al. |
| 2005/0137544 A1 | 6/2005 | Schroeder et al. |
| 2005/0148962 A1 | 7/2005 | Warren et al. |
| 2005/0154362 A1 | 7/2005 | Warren et al. |
| 2005/0283129 A1 | 12/2005 | Hammons et al. |
| 2006/0019056 A1* | 1/2006 | Turner et al. .................. 428/85 |
| 2006/0019063 A1 | 1/2006 | Kelly |
| 2006/0087053 A1 | 4/2006 | O'Donnell et al. |
| 2006/0111684 A1 | 5/2006 | Berba et al. |
| 2006/0184150 A1 | 8/2006 | Noel |
| 2007/0116926 A1 | 5/2007 | Hoying et al. |
| 2008/0154226 A9 | 6/2008 | Hammons et al. |

OTHER PUBLICATIONS

Office Action for U.S. Appl. No. 11/880,931 dated Jun. 12, 2009; Hammons et al.; filed Jul. 25, 2007.

Office Action for U.S. Appl. No. 11/880,931 dated Dec. 24, 2008; Hammons et al.; filed Jul. 25, 2007.

Office Action for U.S. Appl. No. 11/880,931 dated Sep. 14, 2009; Hammons et al.; filed Jul. 25, 2007.

* cited by examiner

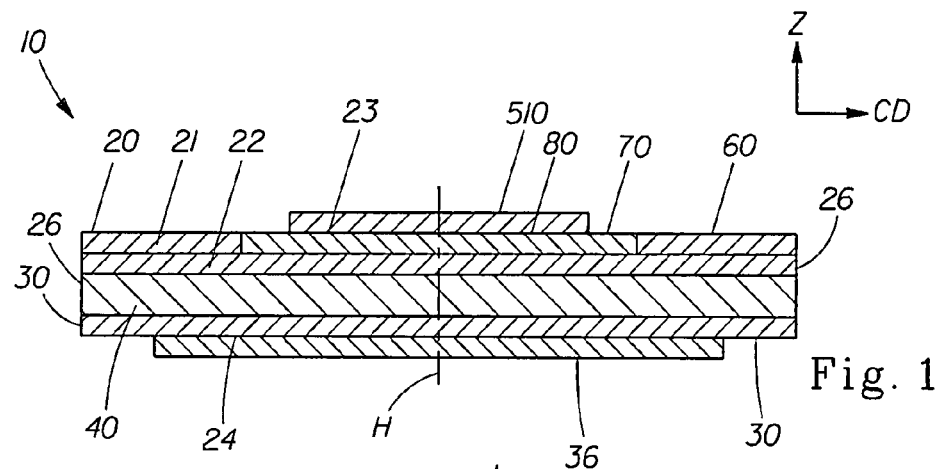
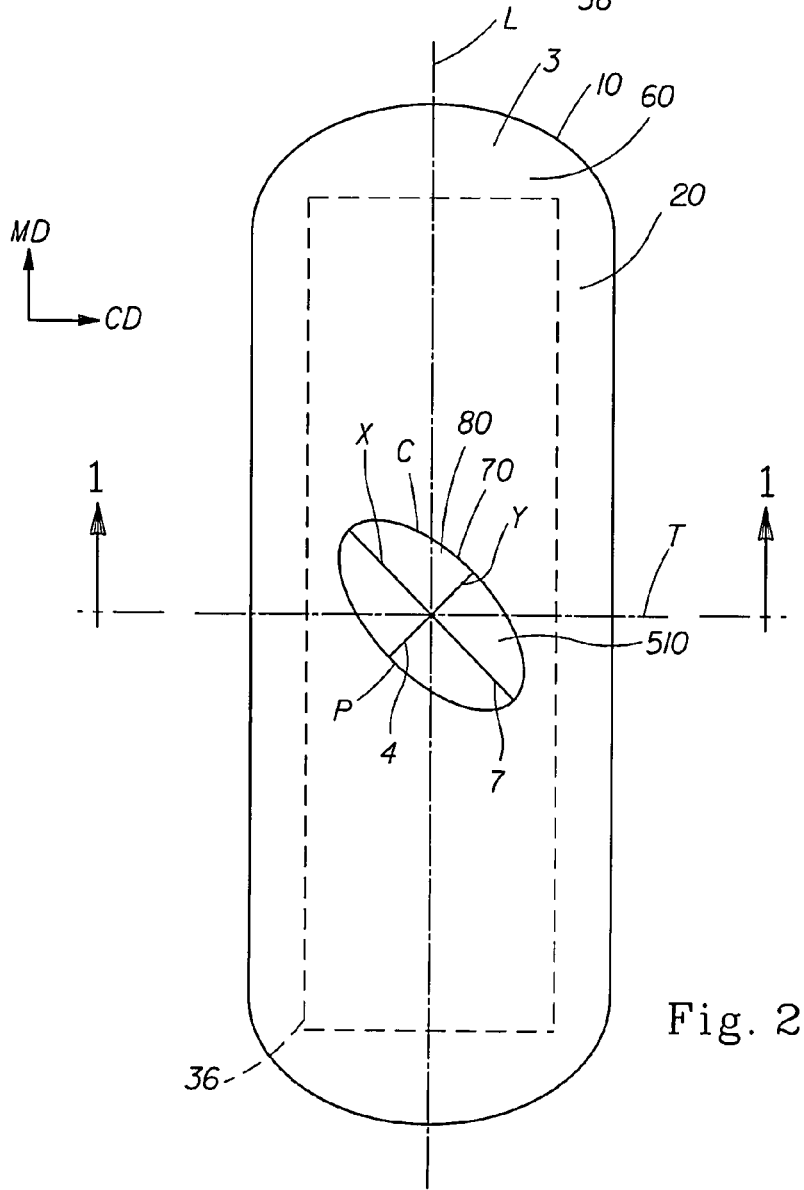
Fig. 1
Fig. 2

ABSORBENT ARTICLE

FIELD OF THE INVENTION

The present invention relates to a topsheet for an absorbent article.

BACKGROUND OF THE INVENTION

Absorbent articles such as sanitary napkins, diapers, adult incontinence products, and the like are designed to be worn in close proximity to the crotch of the wearer. Some absorbent articles, such as sanitary napkins and adult incontinence products are designed to be affixed to the wearer's undergarment so as to remain proximal the wearer's genitals and/or anus. Other absorbent articles, such as diapers and diaper-like adult incontinence products, are designed with a belt-like system that anchors the absorbent article about the wearer's waist. In either configuration, as the wearer moves about his or her daily life, the absorbent article may shift relative to the wearer's body which results in the location of fluid entry into the plan of the absorbent article moving and may result in uncomfortable rubbing forces generated between the wearer and the absorbent article.

The human crotch region can be comprised of many different types of tissues. For instance, in women, the skin of the woman's labia can have a different texture than the skin in her pubic region or anal region. The labia of a woman wearing a sanitary napkin can be particularly sensitive to rubbing forcing created as the woman moves about her daily life. Thus, different portions of a woman's crotch are believed to have different needs related to skin care and comfort.

The shape of the source of fluid to be collected from the human crotch can also vary. For instance, for males, the source of urine is a small discrete opening of the urethra in the penis. As a male wearing a diaper moves, the location of the urethral opening can change relative to the location of the diaper, for instance as the diaper slides around, or as penis changes orientation depending on body orientation, for instance standing versus lying on ones back or side. That is, the location of fluid entry into the diaper can change.

In women, the vagina is a source of fluids such as menses. The opening of the vagina can be generally elongated from the woman's front to rear. The labia minora and labia majora are also generally aligned from the woman's front to back and surround the opening of the vagina. As a woman wearing a sanitary napkin moves, such as by walking, the location from which the vaginal fluid exits the labia majora may move relative to the location of the sanitary napkin. Thus, the location of fluid entry into the sanitary napkin can change.

In some absorbent articles worn in the crotch region, the topsheet, which is proximal the wearer's body and can come into contact with the wearer's body, is designed such that characteristics of one portion of the topsheet differ from the characteristics of other portions. For instance, certain portions of the topsheet of the absorbent article may be configured for collecting fluids and other portions may be configured to provide for comfort while wearing. For many materials commonly used in topsheets, optimizing the material for one performance characteristic, such as fluid acquisition, can result in adverse effects on other performance characteristics, such as comfort. For instance, topsheets having large apertures may acquire fluid more readily than a topsheet having small apertures but a topsheet having small apertures may retain fluid more effectively than a topsheet having large apertures when the absorbent article is compressed. Balancing tradeoffs in different aspects of performance can be difficult, particularly in light of the way in which the absorbent article moves relative to the wearer's body or portions thereof.

In light of the above, there is a continuing unaddressed need for an absorbent article comprising a topsheet of which a portion or portions are configured to deliver one performance benefit and another portion or portions are configured to deliver another performance benefit, the two configured portions being related to one another to achieve improved overall performance.

SUMMARY OF THE INVENTION

An absorbent article that can comprise a topsheet comprising a first portion and a second portion. The absorbent article can have a longitudinal centerline, a transverse centerline, and an area. The second portion can differ in structure from the first portion. The second portion can comprise a structurally modified zone and or a lotion zone having a periphery, a length, and a long axis, the length being a maximum straight-line dimension between two points on the periphery and the long axis extending between two points on the periphery separated by the length. The second portion can comprise a lotion. The periphery can be arranged such that the periphery is not symmetric about an axis parallel to the longitudinal centerline. The long axis of the structurally modified zone can be asymmetric to the longitudinal centerline and the transverse centerline. The structurally modified zone can comprises more than about 5% of the area of said topsheet. The absorbent article can comprise a lotion zone comprising lotion, the long axis of which is asymmetric to the longitudinal centerline and the transverse centerline. The lotion zone can comprise more than about 5% of the area of the topsheet.

BRIEF DESCRIPTION OF THE DRAWINGS

FIG. 1 is a cross section of an absorbent article as indicated by Section 1-1 in FIG. 2.

FIG. 2 is a plan view of the body-facing surface of an absorbent article having a first portion and a second portion.

DETAILED DESCRIPTION OF THE INVENTION

Figure 3:
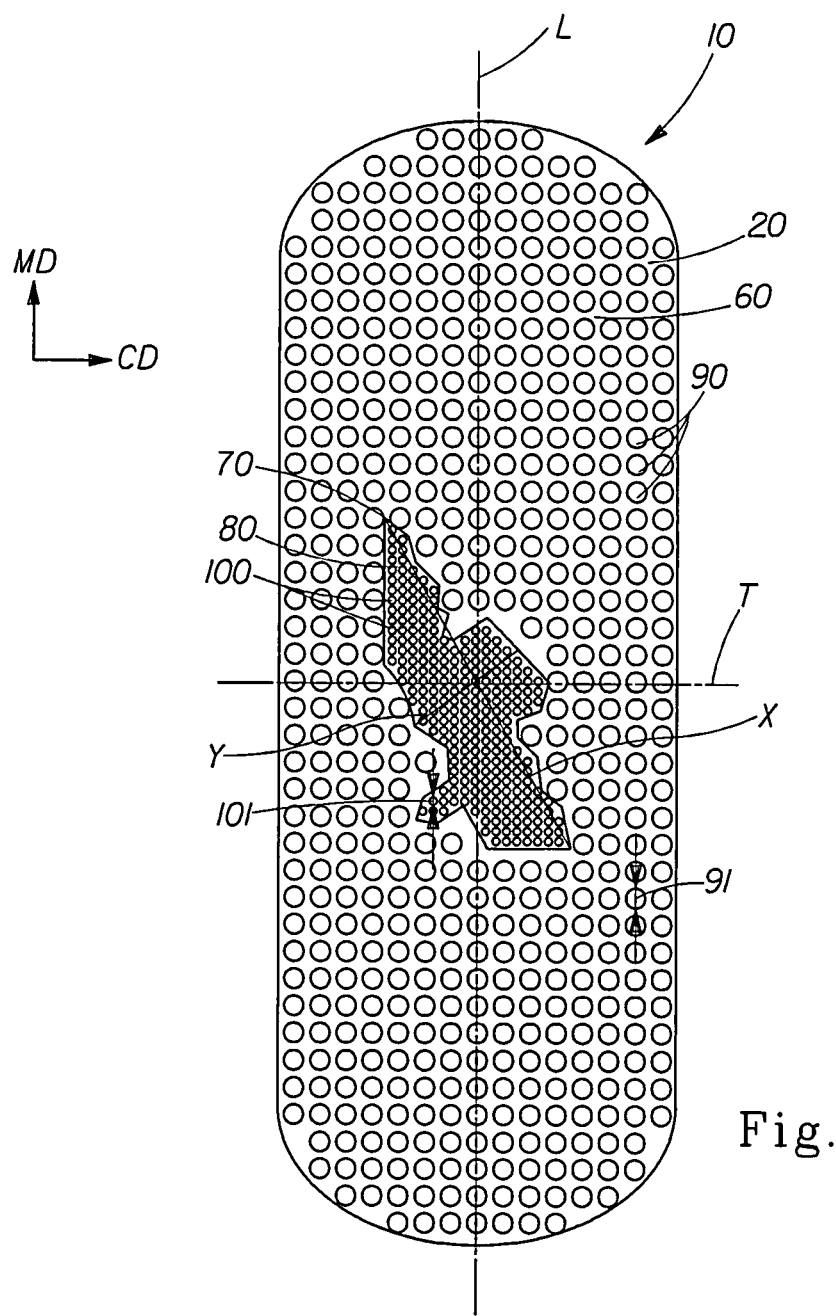
FIG. 3 is a plan view of the body-facing surface of an absorbent article having a first portion and a second portion.

As used herein, "structurally modified", with respect to constituent materials, means that the constituent material (or materials) is altered such that a material that is structurally modified differs in mechanical behavior as compared to the unmodified material. For instance, the structurally modified material can transmit stress (or deform) differently than the unmodified material. The structure of the material can be altered on a molecular level and/or by disrupting the continuity and/or physical arrangement of portions of the material. "Structure" refers to physical arrangement of the constituent material that governs mechanical behavior (e.g. how stress is transmitted through the material).

As used herein, a structurally modified zone is not a channel. As used herein, a "channel" is an indentation having an in-plane length greater than the width, the length being the longest dimension, curved or straight, within the indentation and the in-plane width being the shortest dimension of the indentation. As used herein, a structurally modified zone does not comprise indentations, dimples, or embossments, i.e., structure created by compressing portions of the absorbent article. A structurally modified zone includes, but is not limited to, apertures and tufts.

As used herein, the word "zone" refers to an area set off as distinct from surrounding or adjoining areas. Thus, for example, a topsheet comprising uniformly spaced apertures, each of which are the same size, over the entire surface of the topsheet cannot be considered to have any zones of apertures. Moreover, for example, in a topsheet comprising uniformly spaced apertures, each of which are the same size, a single aperture and locally surrounding material cannot be considered a zone of apertures because that single aperture and locally surrounding material are not distinct from surrounding or adjoining areas. Similarly, for example, a topsheet comprising uniformly spaced elements, each element being the same, over the entire surface of the topsheet cannot be considered to have any zones of elements. Nor, in a topsheet comprising uniformly spaced elements, for example, may a single element and locally surrounding material be considered a zone. A non-limiting example of a zone is a cluster of apertures having one geometric characteristic, such as diameter, set of as distinct from another cluster of apertures having a differing geometric characteristic, such as a different diameter.

As used herein, "elements" are discrete portions of the constituent material that are structurally disrupted. Examples of an element include, but are not limited to, an aperture and a tuft. An indentation, dimple, or embossment, i.e., structure created by compressing portions of the absorbent article, is not an element.

As used herein, two elements are "integral" with one another provided that the elements are formed from the same precursor material or precursor materials. A lotion applied to a topsheet is not integral with the topsheet, as the lotion and topsheet are not formed from the same precursor materials.

As used herein, a "difference in color" refers to a difference or visual distinction in color as characterized by the CIE LAB scale. Differences in color can be measured using a Hunter Color reflectance meter available from Hunter Associates Laboratory, Inc., Reston, Va.

As used herein, "area density" refers to the number of features per unit area. The features can be macrofeatures or microfeatures, as described herein.

As used herein, two objects are "engaged" with one another when stress can be transmitted from one object to the other object.

As used herein, the term "nonwoven web" refers to a web having a structure of individual fibers or threads which are interlaid, but not in a repeating pattern as in a woven or knitted fabric, which do not have randomly oriented fibers. Nonwoven webs or fabrics can be formed from many known processes, such as, for example, air laying processes, meltblowing processes, spunbonding processes, hydroentangling processes, spunlacing processes, and bonded carded web processes. Also, multi-layer webs, such as spunbond-meltblown-spunbond webs and the like made by multiple beam spunbond processes, can be used.

As used herein, the term "polymer" is used in its conventional meaning, and generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries. In general, any of the known polymer types can be used, for example, polyolefinic polymers such as polypropylene or polyethylene can be used either as monocomponent fibers or bicomponent fibers. Other polymers such as PVA, PET polyesters, metallocene catalyst elastomers, nylon and blends thereof can be used. Any or all of the polymers can be cross-linked if desired.

The embodiments disclosed herein are representative of embodiments suitable for use in diapers, sanitary napkins, and adult incontinence articles.

FIG. 1 is an illustration of a cross section of an embodiment of an absorbent article 10 comprising a topsheet of which a portion is configured to deliver one performance benefit and another portion is configured to deliver another performance benefit, the two configured portions being related to one another to achieve optimum overall performance. The absorbent article 10 can comprise a liquid pervious topsheet 20, a fluid impervious backsheet 30, and an absorbent core 40 disposed between the topsheet 20 and backsheet 30. The topsheet 20 can be a composite topsheet 20 comprised of an upper layer 21 and a lower layer 22 that are engaged with one another in a layered relationship. The absorbent article 10 is discussed herein in the context of what is commonly referred to in the art as a sanitary napkin, menstrual pad, or catamenial pad. It is to be understood that the absorbent article 10 can also be any absorbent article designed to be worn in proximity with the crotch of the wearer. The absorbent article can be a consumer product selected from the group consisting of a sanitary napkin, an adult incontinence product, and a diaper.

The absorbent article can be any absorbent article, including, but not limited to, sanitary napkins, adult incontinence products, diapers, body wipes, household wipes, and floor wipes, or an absorbent article used to acquire or dispense fluid. An example of a diaper can be found in U.S. Pat. No. 5,968,025 issued to Roe et al.

The absorbent article 10 and each layer or component thereof can be described as having a body facing surface and a garment facing surface. As can be understood by considering the ultimate use for absorbent articles, such as sanitary napkins, diapers, incontinent products and the like, the body facing surfaces are the surfaces of the layers or components that are oriented closer to the body when in use, and the garment facing surfaces are the surfaces that are oriented closer to the undergarment of the wearer when in use. Therefore, for example, the topsheet 20 has a body facing surface 23 (that can actually be a body contacting surface) and a garment facing surface that can be adhered to an underlying secondary topsheet, such as lower layer 22. The garment facing surface 24 of the backsheet 30, for example, can be oriented closest to, and can contact the wearer's panties in use (via a positioning adhesive 36 if used).

The absorbent article 10 has an absorbent article width measured between the lateral edges 26 measured in the cross-machine direction CD. The absorbent article 10 has a vertical axis H. The absorbent article 10 has a thickness measured in the z-direction.

The topsheet 20 can be comprised of a first portion 60 and a second portion 70. The first portion 60 can differ in structure from the second portion 70. The second portion 70 can comprise a structurally modified zone 80. The second portion 70 can be bound in the machine direction (MD) cross-machine direction (CD) plane by the first portion 60. The second portion 70 can comprise a lotion 510.

As shown in FIG. 2, the topsheet 20 can have a longitudinal centerline L and a transverse centerline T. Longitudinal centerline L and transverse centerline T define a two-dimensional plane of the topsheet 20 prior to use, which, in the embodiment shown, is associated with MD and CD directions as is commonly known in the art of making articles in production lines. The area 3 of the topsheet 20 is in the MD-CD plane. The topsheet 20 can comprise cellulosic material.

As shown in FIG. 2, the structurally modified zone 80 has a periphery P, a length X, and a long axis 7. The length X is the maximum straight-line dimension between two points on the periphery P. The long axis 7 extends between two points on the periphery P separated by the length X. The structurally modified zone 80 has a width Y. The width Y is the maximum dimension between two points on the periphery P measured orthogonal to the length X. The length X is greater than the width Y. The short axis 4 extends between two points on the periphery P measured orthogonal to the long axis and separated by the width Y. The long axis 7 of the structurally modified zone 80 is asymmetric to the longitudinal centerline L of the topsheet. The structurally modified zone 80 can be shaped such that a line drawn between any two points on the periphery P does not cross the periphery P. Further, the structurally modified zone 80 can be shaped such that the long axis 7 is unique in that the structurally modified zone 80 has only one long axis 7.

The first portion 60 and the second portion 70 can be comprised of the same precursor material or materials. A continuous web of material can be comprised of a single unitary web.

The length X can be more than about 1.2 times the width Y. The length X can be more than about 1.5 times the width Y. The length X can be more than about 2 times greater than the width Y.

The structurally modified zone 80 in the second portion 70 can be bounded in the MD-CD plane by the first portion The topsheet 20 has a topsheet length, which is the longest dimension measured parallel to the longitudinal centerline L. The topsheet 20 has a topsheet width, which is the dimension measured in the CD, e.g., parallel to the transverse centerline T. The transverse centerline T intersects the longitudinal centerline L at mid-length of the longitudinal centerline L. The width of the topsheet 20 can vary or be substantially constant along the length of the absorbent article 10. For descriptive purposes, the absorbent article 10 has a longitudinal centerline and transverse centerline taken to be coincident with the longitudinal centerline L and transverse centerline T of the topsheet 20, respectively. The actual longitudinal centerline and the transverse centerline of the absorbent article 10 need not be coincident with the longitudinal centerline L and transverse centerline T of the topsheet 20. The absorbent article 10 has a MD and CD coincident with the machine direction and cross machine direction of the topsheet 20. The topsheet 20 has a vertical axis that can be taken to be coincident with the vertical axis H of the absorbent article 10.

The absorbent article 10 can have strips of positioning adhesive 36 on the garment facing surface 24 of the backsheet 30. The positioning adhesive can be hot-melt adhesive material capable of establishing a temporary bond with the undergarment material. A suitable material is the composition designated HL-1491 XZP commercially available from H. B. Fuller, Toronto, Ontario, Canada.

Without being bound by theory, it is thought that by orienting the first portion 70 such that the long axis 7 is asymmetric to the longitudinal axis L of the topsheet 20, that the second portion 70 can more effectively provide improved fluid acquisition and provide for wearing comfort for particular portions of the wearer's body. For instance, for an absorbent article 10 that is a sanitary napkin, if the second portion 70 is generally located proximal the wearer's vagina, a second portion 70 having a physical structure suited for rapid fluid acquisition oriented as described above and a first portion 60 having a physical structure suited for fluid retention so as to prevent rewet can provide for improved fluid acquisition and retention. It is thought that an asymmetrically oriented second portion 70 provides for an improved chance that at least a portion of the second portion 70 will at times be aligned with the vagina, which is a source of fluid, as the sanitary napkin moves in the wearer's crotch region relative to the wearer's body. Similarly, for adult incontinence products and diapers, the second portion 70 may at times be aligned with the urethra, for urinary incontinence, or the anus, for fecal incontinence. That is, for a human crotch region that is generally symmetric about the sagittal plane (i.e. left and right halves are symmetric), an absorbent article having a second portion 70 that is asymmetric relative to the plane of symmetry of the wearer's body may provide for an improved chance that at least a portion of the second portion 70 will at times be aligned with the desired location of wearer's body.

It is further thought that an asymmetrically oriented second portion 70 allows for a reduced area of the second portion 70 to be used in the sanitary napkin, which can be important because enhancing portions of the topsheet for properties such as fluid acquisition can result in those same portions being degraded with respect to other properties such as rewet and comfort. Similarly, it is thought that a second portion 70 providing for other benefits such as comfort or health of the skin can be oriented asymmetric relative to the longitudinal axis L on other locations of the absorbent article 10 to provide for similar balance between benefits and detriments of particular portions of the topsheet 20 and a greater likelihood that portions of the absorbent article 10 having particular properties, including physical structure, will be proximal portions of the wearer's body where a benefit is targeted.

The structurally modified zone 80 can be described as being integral with the topsheet 20. That is, the topsheet 20 is comprised of the structurally modified zone 80. The structurally modified zone 80 and first portion 60 can be comprised of a continuous web or webs of material. The structurally modified zone 80 and first portion 60 can be comprised of the same precursor materials. The structurally modified zone 80 and the first portion 60 can be comprised of two or more layers engaged with one another. The longitudinal centerline L, transverse centerline T, long axis 7, and short axis 4 can intersect one another at a single point. The intersection of the long axis 7 and short axis 4 of structurally modified zone 80 need not coincide with the intersection of the longitudinal centerline L and the transverse centerline T, as shown in FIG. 2.

The structurally modified zone 80 can be symmetric about the length of the structurally modified zone 80.

The long axis 7 of the structurally modified zone 80 can be more than about 10 degrees out of symmetry with the longitudinal centerline L. The long axis 7 of the structurally modified zone 80 can be more than about 15 degrees out of symmetry with the longitudinal centerline L. The long axis 7 of structurally modified zone 80 can be more than about 30 degrees out of symmetry with the longitudinal centerline L. The long axis 7 of the structurally modified zone 80 can be more than about 40 degrees out of symmetry with the longitudinal centerline L. By out of symmetry, it is meant that the long axis 7 of the structurally modified zone 80 is not parallel to the longitudinal centerline L of the topsheet. The long axis 7 and longitudinal centerline L can be considered to have a vertex, the angle between the long axis 7 and longitudinal centerline L being the magnitude by which the long axis 7 is out of symmetry with the longitudinal centerline L.

The long axis 7 of the structurally modified zone 80 can be more than about 10 degrees out of symmetry with the transverse centerline T. The long axis 7 of the structurally modified zone 80 can be more than about 15 degrees out of symmetry with the transverse centerline T. The long axis 7 of structurally modified zone 80 can be more than about 30 degrees out of symmetry with the transverse centerline T. The long axis 7 of the structurally modified zone 80 can be more than about 40 degrees out of symmetry with the transverse centerline L. By out of symmetry, it is meant that the long axis 7 of the structurally modified zone 80 is not parallel to the transverse centerline T of the topsheet. The long axis 7 and transverse centerline T can be considered to have a vertex, the angle between the long axis 7 and transverse centerline T being the magnitude by which the long axis 7 is out of symmetry with the transverse centerline T.

The long axis 7 and short axis 4 can be out of symmetry with the longitudinal centerline L and transverse centerline T, respectively. The long axis 7 and short axis 4 can be out of symmetry by more than about 15 degrees with the longitudinal centerline L and transverse centerline T, respectively. The long axis 7 and short axis 4 can be out of symmetry by more than about 30 degrees with the longitudinal centerline L and transverse centerline T, respectively.

In one alternative embodiment, the structurally modified zone 80 is not a circle. In another alternative embodiment, the structurally modified zone 80 is not a square. In another alternative embodiment, the structurally modified zone 80 is not a rectangle. In another embodiment, the structurally modified zone 80 is not a circle, square, or rectangle. In another alternative embodiment, the structurally modified zone 80 is not a quadrilateral. In another alternative embodiment, the structurally modified zone 80 is not a polygon. In another alternative embodiment, the structurally modified zone 80 is not a polygon or circle.

In another alternative embodiment, the periphery P is not symmetric about an axis parallel to the longitudinal centerline L. In another alternative embodiment, the periphery P is not symmetric about an axis parallel to the transverse centerline T. In another alternative embodiment, the periphery P is not symmetric about an axis parallel to the longitudinal centerline L and the periphery P is not symmetric about an axis parallel to the transverse centerline T.

The structurally modified zone 80 can comprise more than about 2% of the topsheet area, the area being measured in the plane of the longitudinal centerline L and transverse centerline T of the topsheet 20. The structurally modified zone 80 can comprise more than about 5% of the topsheet area. The structurally modified zone 80 can comprise more than about 10% of the topsheet area. The structurally modified zone 80 can comprise more than about 20% of the topsheet area. The structurally modified zone 80 can comprise more than about 40% of the topsheet area. The structurally modified zone 80 can comprise more than about 50% of the topsheet area. The structurally modified zone 80 can comprise more than about 70% of the topsheet area.

The fluid acquisition rate of the structurally modified zone 80 can be greater than the fluid acquisition rate of the first portion 60. The fluid acquisition rate of the structurally modified zone 80 can be more than about 2 times greater than the fluid acquisition rate of the first portion 60. Fluid acquisition rate can be measured using a drop test wherein a 0.25 mL of sheep blood is applied to the topsheet 20 adhered to, overlying, and in contact with an absorbent core 40 as found in ALWAYS ULTRA sanitary napkins. Sheep blood is applied using a pipette having an open diameter of 4 mm and measuring the time in seconds that is required for the sheep blood to pass through the topsheet to the underlying core, which is the fluid acquisition rate (reported in seconds). Suitable sheep blood can be obtained from Cleveland Scientific.

The structurally modified zone 80 can comprise macro features. Macro features are elements that are visible to the unaided eye of a person having 20/20 vision from a distance of 30 cm in lighting at least equal to the illumination of a standard 100 watt incandescent white light bulb. Macro features can be elements having an area in the MD-CD plane greater than about 0.25 mm$^2$. Macro features can be elements having an area in the MD-CD plane greater than about 1 mm$^2$. Macro features can be elements having an area in the MD-CD plane greater than about 2 mm$^2$. Macro features can be elements having an area in the MD-CD plane less than about 5 mm$^2$. Macro features can be spaced apart from one another by about 1 mm or greater on center.

By way of example and not to be limiting, a macrofeature can be a single aperture, a single tuft, or a single aperture protruding out of the MD-CD plane. Macrofeatures other than tufts, apertures, and apertures protruding out of the MD-CD plane are contemplated.

A structurally modified zone 80 can comprise micro features. Micro features are elements that are not visible to the unaided eye of a person having 20/20 vision from a distance of 30 cm in lighting at least equal to the illumination of a standard 100 watt incandescent white light bulb.

By way of example and not to be limiting, a microfeature can be a single aperture, a single tuft, or a single aperture protruding out of the MD-CD plane. Microfeatures other than tufts, apertures, and apertures protruding out of the MD-CD plane are contemplated. By way of example, and not to be limiting, a structurally modified zone 80 can comprise apertures or tufts. A structurally modified zone 80 can comprise other elements or structures that provide for skin health and/or improved fluid acquisition.

The first portion 60 can have first apertures 90 and the second portion 70 can have second apertures 100, as shown in FIG. 3. The first apertures 90 can differ from the second apertures 100. The first apertures 90 can differ in structure from the second apertures 100. For instance, a topsheet 20 having large apertures may more readily acquire fluid than a topsheet having small apertures. Conversely, a topsheet having smaller apertures may be less prone to rewet of the topsheet than a topsheet having large apertures. Without being bound by theory, it is thought that materials having different apertures can also interact differently with the wearer's skin.

First apertures 90 and second apertures 100 can be circular openings. Individual first apertures 90 and second apertures 100 can have an area between about $0.1$ mm$^2$ and about $4$ mm$^2$ and any area there between in about $0.1$ mm$^2$ increments. Individual first apertures 90 and second apertures 100 can have an area of about $0.25$ mm$^2$, about $1$ mm$^2$, or about $2$ mm$^2$. Individual first apertures 90 and second apertures 100 can have an area greater than about $0.25$ mm$^2$.

Individual first apertures 90 can have a first size 91 and individual second apertures 100 can have a second size 101. The second size 101 can differ from the first size 91, as shown in FIG. 3. The size of an aperture is the largest dimension of the aperture in the MD-CD plane (presented to the viewer of the topsheet). The second size 101 can be larger than the first size 91. The second size 101 can be smaller than the first size 91.

Figure 4:
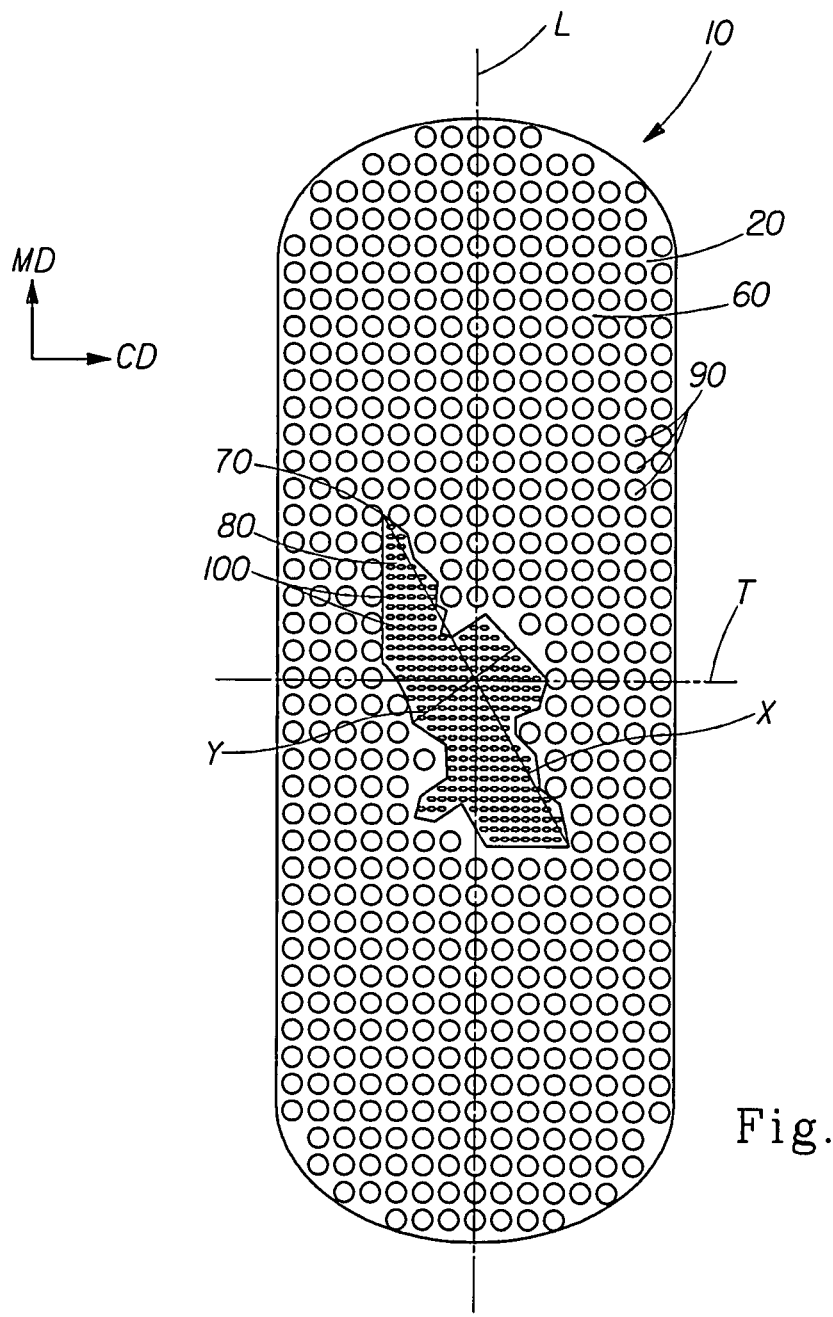
FIG. 4 is a plan view of an absorbent article having a first portion and a second portion.

The in-plane geometry of individual first apertures 90 can differ from the in-plane geometry of individual second apertures 100. In-plane geometry refers to the shape of the object as presented to a viewer looking at the body facing surface 23 of the topsheet 20 so that the MD-CD plane is facing the viewer. For instance, as shown in FIG. 4, first apertures 90 can have a substantially circular shape and the second apertures 100 can have a substantially oval shape. Without being bound by theory, it is thought that the shape of apertures in a material can affect how the material acquires or transmits fluid and how smooth a material is perceived to be. For instance, materials having oval shaped apertures may feel smoother than materials having circular shaped apertures when the material is stroked by a person in a direction parallel to the major axis of the oval shaped apertures even if the minor axis of the oval shaped apertures and diameter of the circular shaped apertures are about the same. Apertures having an oval shape can have a ratio of major axis dimension to minor axis dimension greater than 1. Apertures having an oval shape can have a ratio of major axis dimension to minor axis dimension greater than about 1.5.

The out of plane geometry of the first portion 60 can differ from the out-of-plane geometry of the second portion 70, out-of-plane referring to a direction orthogonal to the MD-CD plane. The in-plane orientation of the topsheet 20 can be defined by the longitudinal centerline L and the transverse centerline T. If the first portion 60 and the second portion 70 comprise apertures, the out-of-plane geometry of individual first apertures 90 can differ from the out-of-plane geometry of individual second apertures 100. Out-of-plane geometry refers the shape presented to a viewer looking at a cross-section of the material orthogonal to the MD-CD plane (or the plane defined by the longitudinal centerline L and transverse centerline T). Out-of-plane geometry can be sensed visually by an observer. In some instances, the out-of-plane geometry of different portions of the topsheet 20 can provide for portions having different fluid acquisition properties and can provide different tactile sensations when different portions of the topsheet 20 are touched. That is, the first portion 60 and second portion 70 of the topsheet 20 can feel different. In the art of garments worn in proximity to the human body, the feel of a material or fabric is referred to as "hand".

Figure 5:
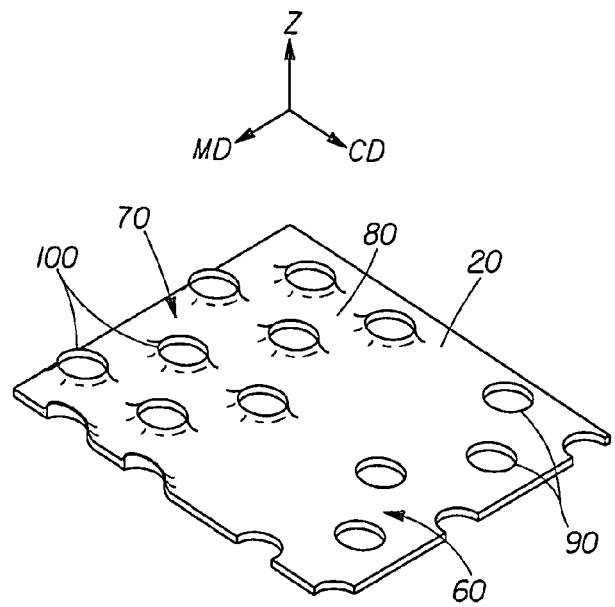
FIG. 5 is a schematic of a portion of a topsheet.

A portion of a topsheet 20 is illustrated in FIG. 5. As shown in FIG. 5, first apertures 90 in the first portion 60 can be substantially flat in the MD-CD plane. Second apertures 100 in the second portion 70 can protrude out of the MD-CD plane in the z direction. Without being bound by theory, a material having apertures protruding out of the MD-CD plane may acquire fluid differently than a material having apertures in plane, depending on the deformability of the material and the geometry of the out-of-plane protrusion and the geometry of the rim of the aperture.

The first portion 60 can have a first portion aperture area density and the second portion 70 can have a second portion aperture area density. The first portion aperture area density can differ from the second portion aperture area density.

The topsheet 20 can be film, a nonwoven, or a laminate. Not to be limiting, a laminate topsheet can comprise two layers of film, two layers of nonwoven, or a layer of nonwoven with a film. Apertures can include micro apertures and macro apertures. Macro apertures are apertures that are visible to the unaided eye of a person having 20/20 vision from a distance of 30 cm in lighting at least equal to the illumination of a standard 100 watt incandescent white light bulb. Macro apertures can be elements having an area in the MD-CD plane greater than about $0.25$ mm$^2$. Micro apertures are apertures that are not visible to the unaided eye of a person having 20/20 vision from a distance of 30 cm in lighting at least equal to the illumination of a standard 100 watt incandescent white light bulb. Micro apertures and/or other texturing can be formed prior to processing as described herein.

Figure 6:
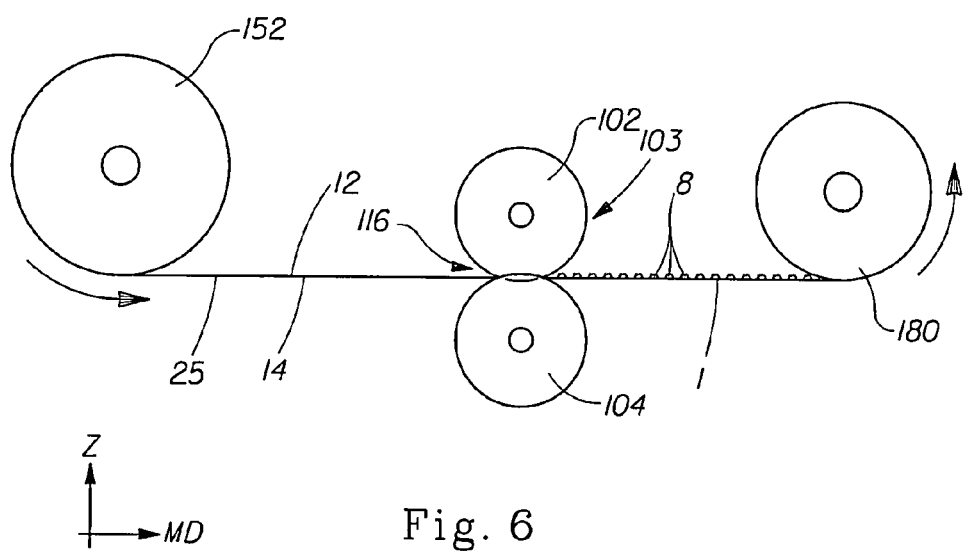
FIG. 6 is a schematic of an apparatus for forming a web having apertures.

An apertured web 1, which can be used as a topsheet 20, can be formed as shown in FIG. 6. As shown in FIG. 6, web 1 can be formed from a generally planar, two dimensional precursor web 25 having a first side 12 and a second side 14. Precursor web 25 can be, for example, a polymer film, a nonwoven web, a woven fabric, a paper web, a tissue paper web, a cellulosic web, or a knitted fabric, or a multilayer laminate of any of the aforementioned. In general, the term "side" is used herein in the common usage of the term to describe the two major surfaces of generally two-dimensional webs, such as paper and films. In a composite or laminate structure, the first side 12 of the web 1 is the first side of one of the outermost layers or plies, and the second side 14 is the second side of the other outermost layer or ply.

Precursor web 25 can be a polymeric film web or a cellulosic web. Polymeric film webs can be deformable. Deformable, as used herein, describes a material which, when stretched beyond its elastic limit, will substantially retain its newly formed conformation. Such deformable materials may be chemically homogeneous or heterogeneous, such as homopolymers and polymer blends, structurally homogeneous or heterogeneous, such as plain sheets or laminates, or any combination of such materials.

Deformable polymeric film webs that can be used can have a transformation temperature range in which changes in the solid state molecular structure of the material occur. Changes in the structure can include a change in crystalline structure and/or a change from solid to molten state. As a consequence, above the transformation temperature range, certain physical properties of the material are substantially altered. For a thermoplastic film, the transformation temperature range is the melt temperature range of the film, above which the film is in a molten state and loses substantially all previous thermo-mechanical history.

Polymeric film webs can comprise thermoplastic polymers having characteristic rheological properties which depend on their composition and temperature. Below their glass transition temperature, such thermoplastic polymers can be hard, stiff, and/or brittle. Below the glass transition temperature, the molecules are in rigid, fixed positions. Above the glass transition temperature but below the melt temperature range, thermoplastic polymers exhibit viscoelasticity. In this temperature range, the thermoplastic material generally has a certain degree of crystallinity, and is generally flexible and to some degree deformable under a force. The deformability of such a thermoplastic is dependent on the rate of deformation, amount (dimensional quantity) of deformation, length of time it is deformed, and its temperature. In one embodiment, processes can be utilized to form materials comprising thermoplastic polymers, especially thermoplastic film, which are within this viscoelastic temperature range.

Polymeric film webs can comprise a certain amount of ductility. Ductility, as used herein, is the amount of permanent, unrecoverable, plastic strain which occurs when a material is deformed, prior to failure (rupture, breakage, or separation) of the material. Materials that can be used as described herein can have a minimum ductility of at least about 10%, or at least about 50%, or at least about 100%, or at least about 200%.

Polymeric film webs can include materials normally extruded or cast as films such as polyolefins, nylons, polyesters, and the like. Such films can be thermoplastic materials such as polyethylene, low density polyethylene, linear low density polyethylene, polypropylenes and copolymers and blends containing substantial fractions of these materials. Such films can be treated with surface modifying agents to impart hydrophilic or hydrophobic properties, such as imparting a lotus effect. As noted below, polymeric film webs can be textured or otherwise altered from a strictly flat, planar configuration.

Precursor web 25 can be a nonwoven web. For nonwoven precursor webs 25, the precursor web 25 can comprise unbonded fibers, entangled fibers, tow fibers, or the like. Fibers can be extensible and/or elastic, and may be pre-stretched for processing. Fibers of precursor web 25 can be continuous, such as those produced by spunbonded methods, or cut to length, such as those typically utilized in a carded process. Fibers can be absorbent, and can include fibrous absorbent gelling materials. Fibers can be bicomponent, multiconstituent, shaped, crimped, or in any other formulation or configuration known in the art for nonwoven webs and fibers.

Nonwoven precursor webs 25 can be any known nonwoven webs comprising polymer fibers having sufficient elongation properties to be formed into apertured web 1. In general, the polymeric fibers can be bondable, either by chemical bond (e.g. by latex or adhesive bonding), pressure bonding, or thermal bonding. If thermal bonding techniques are used in the bonding process described below, a certain percentage of thermoplastic material, such as thermoplastic powder or fibers can be used to facilitate thermal bonding of portions of fibers in the web, as discussed more fully below. Nonwoven precursor web 25 can comprise about 100% by weight thermoplastic fibers. Nonwoven precursor web 25 can comprise as little as about 10% by weight thermoplastic fibers. Likewise, nonwoven precursor web 25 can comprise any amount by weight thermoplastic fibers in 1% increments between about 10% and about 100%.

Precursor web 25 can be a composite or a laminate of two or more precursor webs, and can comprise two or more nonwoven webs or a combination of polymer films, nonwoven webs, woven fabrics, paper webs, tissue webs, or knitted fabrics. Precursor web 25 can be supplied from a supply roll 152 (or supply rolls, as needed for multiple web laminates) or any other supply means, such as festooned webs, as is known in the art. In one embodiment, precursor web 25 can be supplied directly from a web making apparatus, such as a polymer film extruder or a nonwoven web-making production line.

The total basis weight of precursor web 25 (including laminate or multi-layer precursor webs 25) can range from about 8 gsm to about 500 gsm, depending on the ultimate use of the web 1, and can be produced in 1 gsm increments between about 8 and about 500 gsm. The constituent fibers of nonwoven precursor web 25 can be polymer fibers, and can be monocomponent, bicomponent and/or biconstituent fibers, hollow fibers, non-round fibers (e.g., shaped (e.g., trilobal) fibers or capillary channel fibers), and can have major cross-sectional dimensions (e.g., diameter for round fibers, long axis for elliptical shaped fibers, longest straight line dimension for irregular shapes) ranging from 0.1-500 microns in 0.1 micron increments.

Precursor web 25 can be preheated by means known in the art, such as by radiant heating, forced air heating, convection heating, or by heating over oil-heated rollers. Precursor web 25 can be treated with coatings, such as with surfactants, lotions, adhesives, and the like. Treating precursor web 25 can be achieved by means known in the art such as by spraying, slot coating, extruding, or otherwise applying coatings to one or both surfaces.

Supply roll 152 rotates in the direction indicated by the arrow in FIG. 6 as precursor web 25 is moved in the machine direction by means known in the art, including over or around any of various idler rollers, tension-control rollers, and the like to the nip 116 of a pair of counter-rotating rolls 102 and 104. The rolls 102 and 104 can comprise forming apparatus 103. The pair of rolls 102 and 104 can operate to form truncated generally conical shaped structures 8 and apertures in precursor web 25. Apertured web 1 can be taken up on wind up roll 180.

There are a variety of approaches for creating apertures in webs. Factors that can influence the approach selected for creating apertures include, but are not limited to, whether the precursor web 25 is a nonwoven or polymeric film, the desired geometry of the aperture, the desired processing speed, and the amount of control of the process that is desired.

Figure 7:
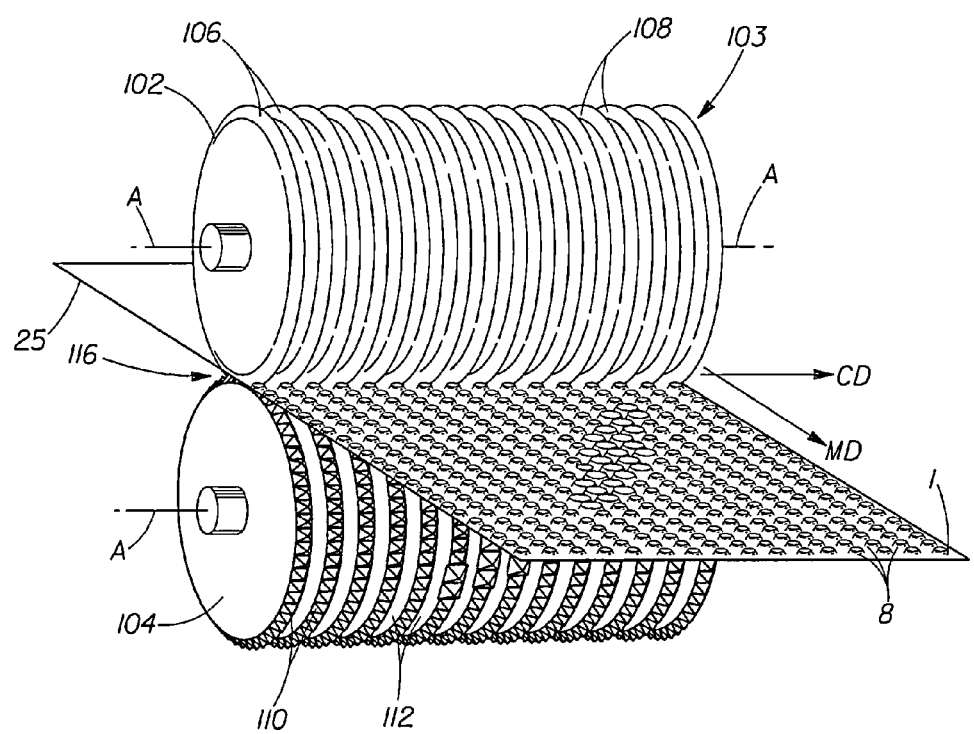
FIG. 7 is a schematic of an apparatus for forming a web having apertures.

An approach for forming apertures in polymeric film webs and nonwoven webs is to employ a pair of intermeshing rolls 102 and 104, as shown in FIG. 7 and disclosed in U.S. patent application Ser. No. 11/249,618 by O'Donnell et al. Referring to FIG. 7, there is shown in more detail the portion of the apparatus shown in FIG. 6 that can form apertured web 1. Forming apparatus 103 can comprise a pair of steel (or other suitably hard material) intermeshing rolls 102 and 104, each rotating about an axis A, the axes A being parallel and in the same plane. Forming apparatus 103 can be designed such that precursor web 25 remains on roll 104 through a certain angle of rotation. FIG. 7 shows in principle what happens as precursor web 25 goes straight through nip 116 on forming apparatus 103 and exits as apertured web 1. Precursor web 25 or apertured web 1 can be partially wrapped on either of rolls 102 or 104 through a predetermined angle of rotation prior to (for precursor web 25) or after (for web 1) nip 116.

Roll 102 can comprise a plurality of ridges 106 and corresponding valleys 108 which can extend unbroken about the entire circumference of roll 102. Depending on what kind of pattern is desired in apertured web 1, roll 102 can comprise ridges 106 wherein portions have been removed, such as by etching, milling or other machining processes, such that some or all of ridges 106 are not circumferentially continuous, but have breaks or gaps. Ridges 106 can be spaced apart from one another along the axis A of roll 102. For instance, the middle third of roll 102 can be smooth and the outer thirds of roll 102 can have a plurality of ridges that are spaced apart from one another. Similarly, ridges 106 on the middle third of roll 102 can be spaced more closely together than ridges 106 on the outer thirds of roll 102. The breaks or gaps, in either the circumferential direction, axial direction, or both directions, can be arranged to form a pattern, including geometric patterns such as circles or diamonds. In one embodiment, roll 102 can have teeth, similar to the teeth 110 on roll 104, described below. In this manner, it is possible to have three dimensional apertures having portions extending outwardly on both sides of apertured web 1.

Roll 104 can comprise a plurality of rows of circumferentially-extending ridges that have been modified to be rows of circumferentially-spaced teeth 110 that extend in spaced relationship about at least a portion of roll 104. The individual rows of teeth 110 of roll 104 can be separated by corresponding grooves 112. In operation, rolls 102 and 104 intermesh such that the ridges 106 of roll 102 extend into the grooves 112 of roll 104 and the teeth 110 of roll 104 extend into the valleys 108 of roll 102. Both or either of rolls 102 and 104 can be heated by means known in the art such as by incorporating hot oil filled rollers or electrically-heated rollers. Both or either of the rolls may be heated by surface convection or by surface radiation. As shown in FIG. 7, the spacing and size of the teeth 110 can be varied. The spacing and/or size of the teeth 110 and grooves 112 on one portion of the roll 104 can be different from the spacing and/or size of the teeth 110 and grooves 112 on another portion of roll 104. This will allow different portions of an apertured web 1, which can form topsheet 20, to have first and second portions that differ from one another. Portions of roll 104 can be without teeth 110 so that portions of web 1 can be without apertures. As shown in schematic in FIG. 7, truncated generally conical shaped structures 8 can be formed in precursor web 25.

Figure 8:
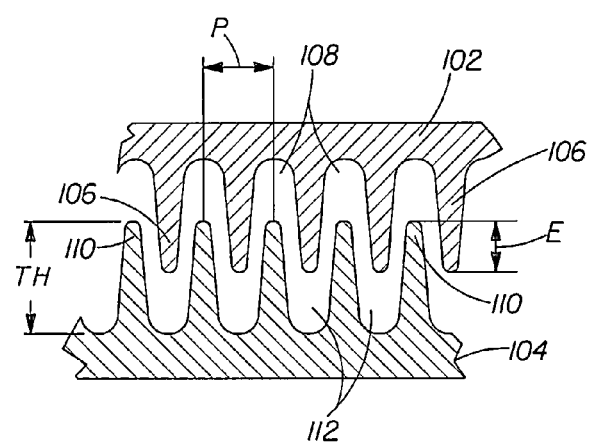
FIG. 8 is a schematic of how the teeth and grooves interengage with one another.

A schematic of a cross section a portion of the intermeshing rolls 102 and 104 including ridges 106 and representative teeth 110 is shown in FIG. 8. As shown, teeth 110 have a tooth height TH (note that TH can also be applied to ridge 106 height and tooth height and ridge height can be equal) and a tooth-to-tooth spacing (or ridge-to-ridge spacing) referred to as the pitch P. As shown, depth of engagement, (DOE) E is a measure of the level of intermeshing of rolls 102 and 104 and is measured from tip of ridge 106 to tip of tooth 110. The depth of engagement E, tooth height TH, and pitch P can be varied as desired depending on the properties of precursor web 25 and the desired characteristics of apertured web 1.

In one embodiment, the dimensions of ridges, grooves, and/or teeth are machined to account for thermal expansion, such that the dimensions shown in FIG. 8 and dimensions described herein are dimensions at operating temperature. The rolls 102 and 104 can be made of wear resistant stainless steel.

The aperture area density can be varied from about 1 aperture/cm$^2$ to about 6 apertures/cm$^2$ to about 60 apertures/cm$^2$, in increments of 1 aperture/cm$^2$. There can be at least about 10 apertures/cm$^2$, or at least about 25 apertures/cm$^2$.

As can be understood with respect to forming apparatus 103, apertures can be made by mechanically deforming precursor web 25 that can be described as generally planar and two dimensional. By "planar" and "two dimensional" is meant simply that the precursor web 25 may be flat relative to a finished apertured web 1 having a distinct, out-of-plane, z-direction three-dimensionality imparted due to the formation of truncated generally conical shaped structures 8. "Planar" and "two-dimensional" are not meant to imply any particular flatness, smoothness or dimensionality and a soft, fibrous non-woven web can be planar in its as-made condition.

As precursor web 25 goes through the nip 116, the teeth 110 of roll 104 enter valleys 108 of roll 102 and simultaneously urge material out of the plane of precursor web 25 to form truncated generally conical shaped structures 8 and apertures, the apertures being defined by the rim of the truncated generally conical shaped structures. In effect, teeth 110 "push" through precursor web 25. As the tip of teeth 110 push through precursor web 25 the web material can be urged by the teeth 110 out of the plane of precursor web 25 and can be stretched and/or plastically deformed in the z-direction, creating out-of-plane geometry characterized by truncated generally conical shaped structures 8 and apertures. The truncated generally conical shaped structures 8 can be thought of as volcano-shaped structures.

Figure 9:
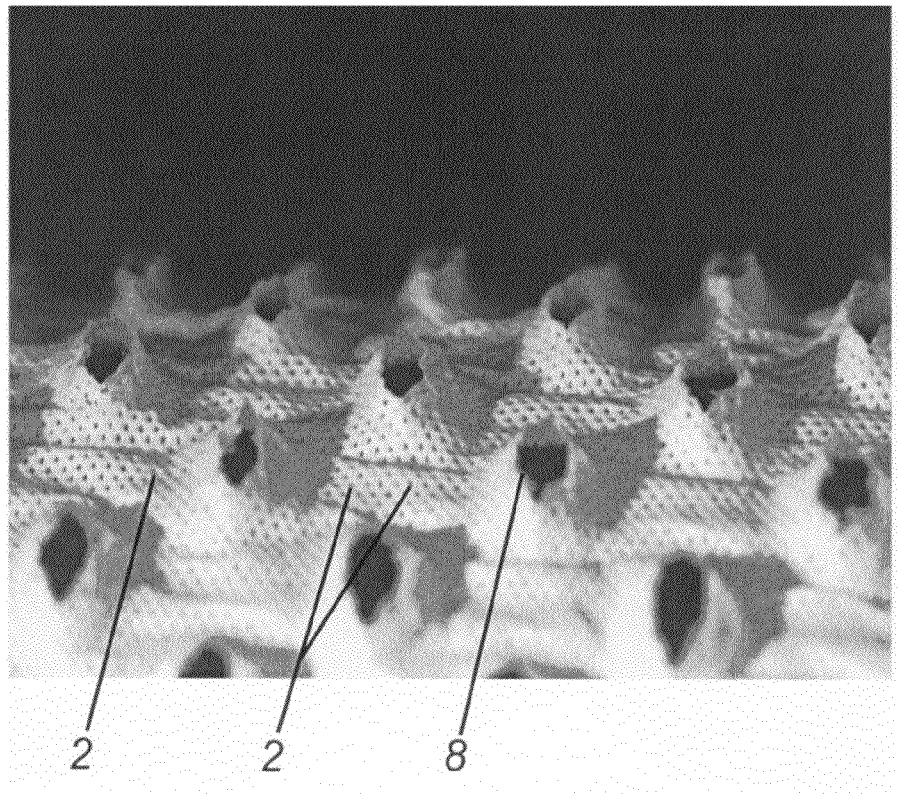
FIG. 9 is an illustration of truncated generally conically shaped apertures and aberrations.

FIG. 9 shows an embodiment of a three-dimensional apertured web 1 in which the precursor web 25 was not a flat film but rather was a film that was pre-textured with microscopic aberrations 2. Aberrations 2 can be bumps, embossments, holes, or the like. In the embodiment shown, aberrations 2 are volcano-shaped micro-apertures, formed by a hydroforming process. A suitable hydroforming process is the first phase of the multiphase hydroforming process disclosed in U.S. Pat. No. 4,609,518, issued to Curro et al. on Sep. 2, 1986. The hydroforming screen utilized for the web shown in FIG. 9 was a "100 mesh" screen and the film was obtained from Tredegar Film Products, Terre Haute, Ind. Apertures, defined by the rims of the truncated generally conical shaped structures 8, can be formed by teeth 110 of roll 104 in forming apparatus 103. The truncated generally conical shaped structures 8 can be oriented in a topsheet 20 such that the rims of the truncated generally conical shaped structures are on the body facing side of the topsheet. The truncated generally conical shaped structures 8 can be oriented in a topsheet 20 such that the rims of the truncated generally conical shaped structures are on the garment facing side of the topsheet 20. The truncated generally conical shaped structures 8 can be oriented in a topsheet 20 such that some of the rims of the truncated generally conical shaped structures are on the garment facing side of the topsheet 20 and some of the rims of the truncated generally conical shaped structures are on the body facing side of the topsheet 20.

Aberrations 2 can also be non-apertured protrusions or fibrils to provide texture that provides for a tactile impression of softness. Aberrations 2 other than non-apertured protrusions and fibrils are contemplated. Softness can be beneficial when webs 1 are used as a topsheet in a disposable absorbent article. A soft, compliant topsheet for a disposable absorbent article can be achieved when the apertured web 1 is used with the second side 14 having aberrations 2 as the body-facing surface of the article. In some embodiments, aberrations 2 can be on the garment facing side of the topsheet to possibly provide for a different level of comfort or different properties related to flow of fluids.

The apertures of the film embodiments shown in FIG. 9 were made on an apparatus like that shown in FIG. 7, where the forming apparatus 103 is arranged to have one patterned roll, e.g., roll 104, and one non-patterned roll 102. In certain embodiments nip 116 can be formed by using two patterned rolls having either the same or differing patterns, in the same or different corresponding regions of the respective rolls. Such an apparatus can produce webs with apertures protruding from both sides of the apertured web 1, as well as macro-texture, e.g., aberrations, micro-apertures, or micro-patterns, in the web 1. Likewise, it may be desirable to have multiple forming apparatuses 103 such that apertured web 1 is re-processed to have additional truncated generally conical shaped structures 8 and/or apertures. For example, a greater aperture area density of truncated generally conical shaped structures 8 on apertured web 1 can be achieved by processing precursor web 25 through two or more forming apparatuses 103 or by decreasing the spacing between teeth 110.

Figure 10:
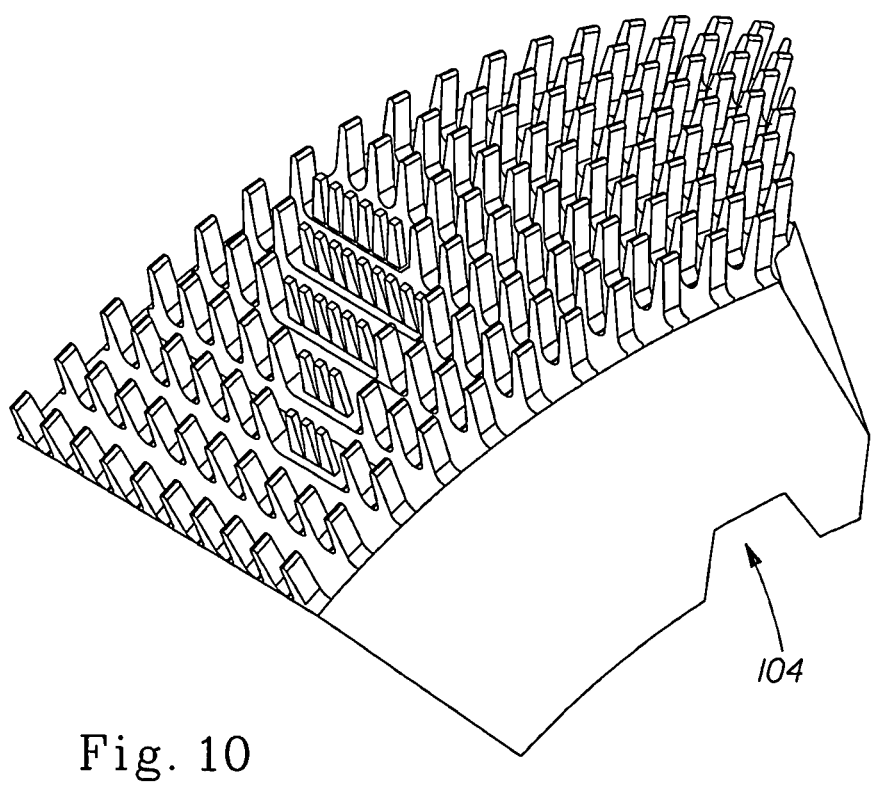
FIG. 10 is a schematic of a roll having different sized teeth and spacing of teeth.

The number, aperture area density, size, geometry, and out of plane geometry associated with the apertures can be varied by changing the number, spacing between, geometry, and size of teeth 110 and making corresponding dimensional changes as necessary to roll 104 and/or roll 102. A topsheet 20 having a first portion 60 having first apertures and second portion 70 having second apertures can be formed using a roll 104 in which different portions of the roll 104 have one size and/or spacing of teeth 110 and other portions of roll 104 have another size and/or spacing of teeth 110. FIG. 10 illustrates a portion of roll 104 in which different areas of the roll 104 have different sizes and/or spacing of teeth 110. Teeth 110 can be generally conical, pyramidal, truncated conical, or truncated pyramidal shaped, or any other suitable shape.

Figure 11:
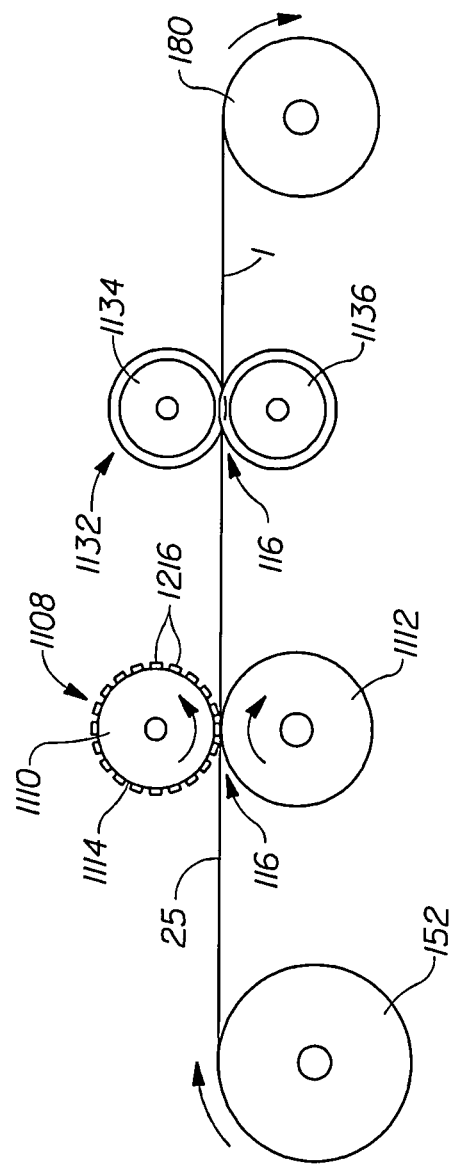
FIG. 11 a schematic of an apparatus for selectively aperturing a nonwoven web.

The topsheet 20 can comprise an apertured nonwoven web. Referring to FIG. 11 there is schematically illustrated a process and apparatus for selectively aperturing a nonwoven web suitable for use as a topsheet on a disposable absorbent article. U.S. patent application Ser. No. 11/249,618, U.S. Pat. Nos. 5,714,107, and 5,628,097 disclose apertures, apparatuses, and methods for creating apertures in nonwoven webs.

Nonwoven precursor web 25 can be unwound from a supply roll 152 and travel in a direction indicated by the arrows associated therewith as the supply roll 152 rotates in the direction indicated by the arrows associated therewith. The nonwoven precursor web 25 passes through a nip 116 of the web weakening roller arrangement 1108 formed by calender roll 1110 and smooth anvil roller 1112.

The nonwoven precursor web 25 may be formed by known nonwoven extrusion processes, such as, for example, known meltblowing processes or known spunbonding processes, and passed directly through the nip 116 without first being bonded and/or stored on a supply roll.

The nonwoven precursor web 25 may be extensible, elastic, or nonelastic. The nonwoven precursor web 25 may be a spunbonded web, a meltblown web, or a bonded carded web. If the nonwoven precursor web 25 is a web of meltblown fibers, it may include meltblown microfibers. The nonwoven precursor web 25 may be made of fiber forming polymers such as, for example, polyolefins. Exemplary polyolefins include one or more of polypropylene, polyethylene, ethylene copolymers, propylene copolymers, and butene copolymers.

In another embodiment, the nonwoven precursor web 25 may be a multilayer material having, for example, at least one layer of a spunbonded web joined to at least one layer of a meltblown web, a bonded carded web, or other suitable material. For example, the nonwoven precursor web 25 may be a multilayer web having a first layer of spunbonded polypropylene having a basis weight from about 0.2 to about 8 ounces per square yard, a layer of meltblown polypropylene having a basis weight from about 0.2 to about 4 ounces per square yard, and a second layer of spunbonded polypropylene having a basis weight from about 0.2 to about 8 ounces per square yard. Alternatively, the nonwoven web may be a single layer of material, such as, for example, a spunbonded web having a basis weight from about 0.2 to about 10 ounces per square yard or a meltblown web having a basis weight from about 0.2 to about 8 ounces per square yard.

The nonwoven precursor web 25 may be joined to a polymeric film to form a laminate. Suitable polymeric film materials include but are not limited to polyolefins, such as polyethylenes, polypropylene, ethylene copolymers, propylene copolymers, and butene copolymers; nylon (polyamide); metallocene catalyst-based polymers; cellulose esters; poly (methyl methacrylate); polystyrene; poly (vinyl chloride); polyester; polyurethane; compatible polymers; compatible copolymers; and blends, laminates and/or combinations thereof.

The nonwoven precursor web 25 may also be a composite made up of a mixture of two or more different fibers or a mixture of fibers and particles. Such mixtures may be formed by adding fibers and/or particulates to the gas stream in which the meltblown fibers or spunbond fibers are carried so that an intimate entangled co-mingling of fibers and other materials, e.g., wood pulp, staple fibers, and particles, occurs prior to collection of the fibers.

The nonwoven precursor web 25 of fibers can be joined by bonding to form a coherent web structure. Suitable bonding techniques include, but are not limited to, chemical bonding, thermobonding, such as point calendering, hydroentangling, and needling.

One or both of the patterned calender roll 1110 and the smooth anvil roller 1112 may be heated and the pressure between the two rollers may be adjusted to provide the desired temperature, if any, and pressure to concurrently weaken and melt-stabilize the nonwoven precursor web 25 at a plurality of locations.

The patterned calender roll 1110 is configured to have a cylindrical surface 1114, and a plurality of protuberances 1216 which extend outwardly from cylindrical surface 1114. The protuberances 1216 are disposed in a predetermined pattern with each protuberance 1216 being configured and disposed to precipitate a weakened, melt-stabilized location in the nonwoven precursor web 25 to create a predetermined pattern of weakened, melt-stabilized locations in the nonwoven precursor web 25. Also shown in FIG. 11 and discussed further below are incremental stretching system 1132, and incremental stretching rollers 1134 and 1136.

Prior to entering nip 116, the coherent nonwoven web comprises a plurality of fibers joined together by point calendered bonds 200 to form a coherent web structure.

Figure 12:
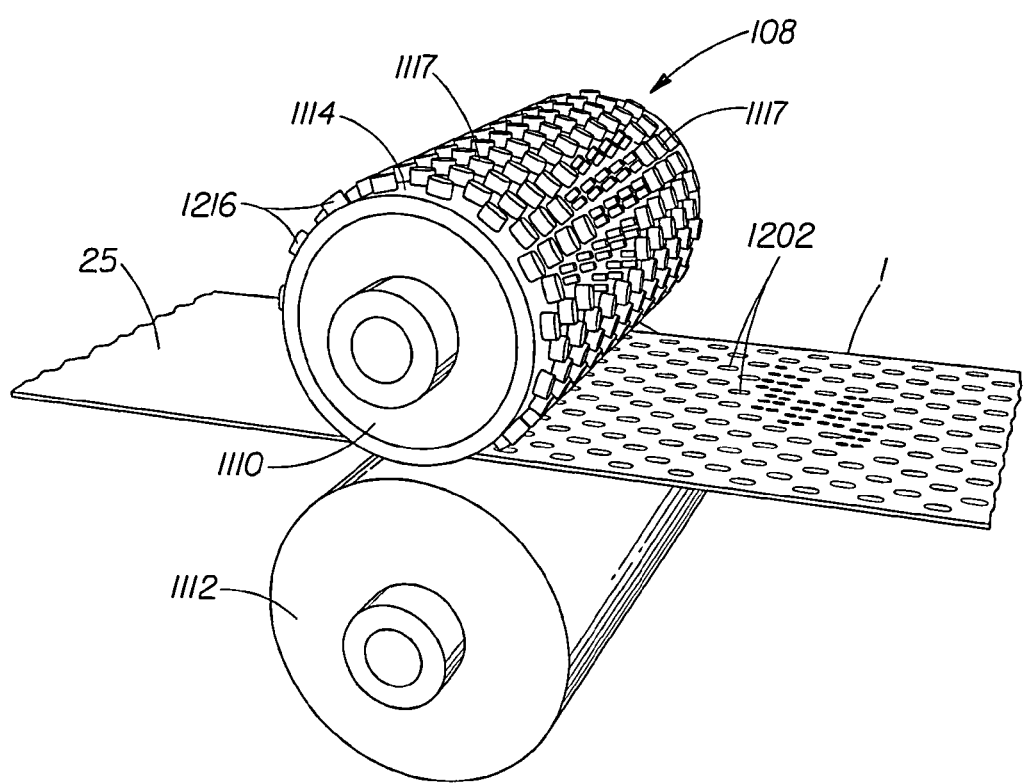
FIG. 12 is a schematic of a weakening roller arrangement.

Patterned calender roll 1110 can have a repeating pattern of protuberances 1216 which extend about the entire circumference of cylindrical surface 1114. Alternatively, the protuberances 1216 may extend around a portion, or portions of the circumference of cylindrical surface 1114. As shown in FIG. 12, the spacing of the protuberances 1216 on one portion of the patterned calender roll 1110 can be different from the spacing of the protuberances 1216 on another part of the patterned calender roll 1110. Arranging the protuberances 1216 in this manner can allow different portions of an apertured web 1, which can form the topsheet 20, to have first and second portions that differ from one another.

By way of example and not to be limiting, protuberances 1216 can be truncated conical shapes which extend radially outwardly from cylindrical surface 1114 and which have elliptical distal end surfaces 1117. Other suitable shapes for distal end surfaces 1117 include, but are not limited to circular, square, rectangular, etc. The patterned calender roll 1110 can be finished so that all of the end surfaces 1117 lie in an imaginary right circular cylinder which is coaxial with respect to the axis of rotation of calender roll 1110.

Protuberances 1216 can be blades having their long axis oriented circumferentially about the patterned calender roll 1110. Protuberances 1216 can be blades having their long axis oriented parallel to the rotating axis of the calender roll 1110.

The protuberances may be disposed in any predetermined pattern about patterned calender roll 1110. After passing through the weakening roller arrangement 1108, the precursor web 25 can have a plurality of melt stabilized locations 1202. Anvil roller 1112, can be a smooth surfaced, right circular cylinder of steel.

Figure 13:
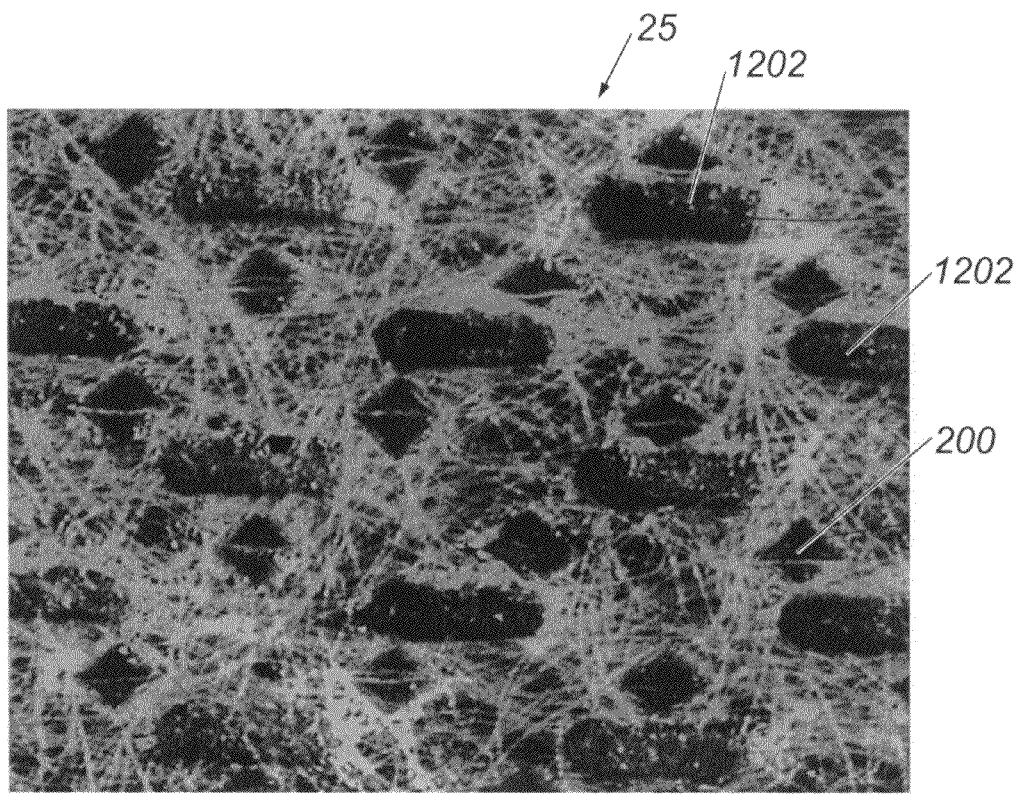
FIG. 13 is an image of a nonwoven web after passing through the weakening roller arrangement.

FIG. 13 is an image of the nonwoven precursor web 25 after having passed through the weakening roller arrangement 1108, and prior to passing through the nip 116 of the incremental stretching system 1132. As can be seen in the image, the nonwoven precursor web 25 includes a plurality of weakened, melt-stabilized locations 1202. Weakened, melt-stabilized locations 1202 generally correspond to the pattern of protuberances 1216 extending from the cylindrical surface 1114 of patterned calender roll 1110. As shown in FIG. 13, the nonwoven precursor web 25 also includes coherent web forming point calendered bonds 200 which serve to maintain the structural integrity of the nonwoven precursor web 25.

From the weakening roller arrangement 1108, the nonwoven precursor web 25 passes through nip 116 formed by the incremental stretching system 1132 employing opposed pressure applicators having three-dimensional surfaces which at least to a degree are complementary to one another.

Figure 14:
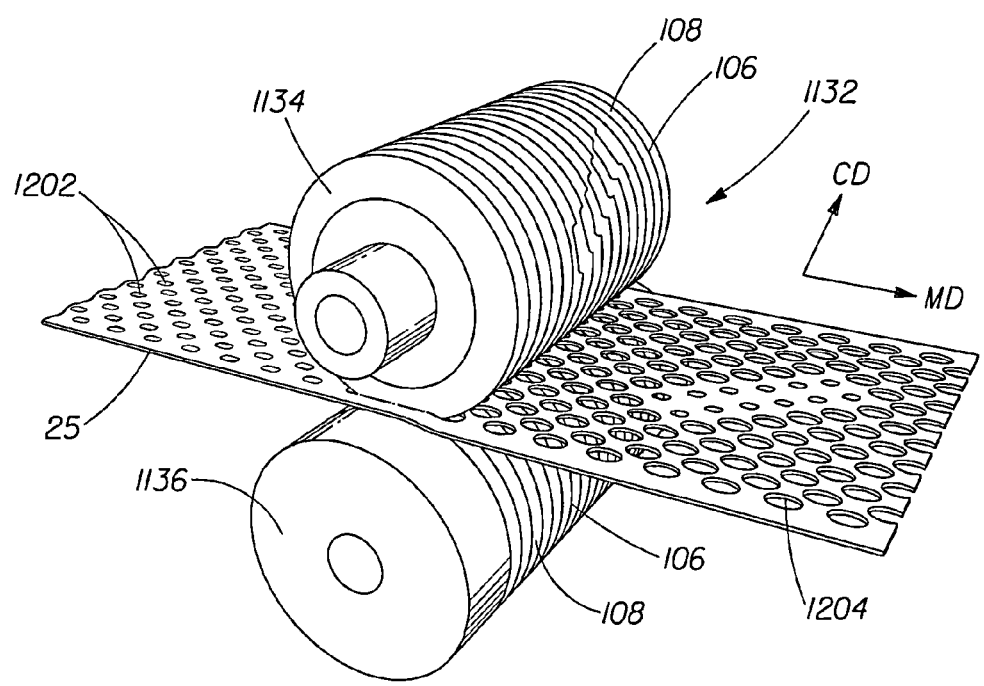
FIG. 14 is a schematic of a stretching system.

Referring now to FIG. 14, there is shown a fragmentary enlarged view of the incremental stretching system 1132 comprising incremental stretching rollers 1134 and 1136. The incremental stretching roller 1134 can comprise a plurality of ridges 106 and corresponding valleys 108 that extend about the entire circumference of incremental stretching roller 1134 or only partially about the circumference of incremental stretching roller 1134. Incremental stretching roller 1136 includes a plurality of complimentary ridges 106 and a plurality of corresponding valleys 108. The ridges 106 on incremental stretching roller 1134 intermesh with or engage the valleys 108 on incremental stretching roller 1136 and the ridges 106 on incremental stretching roller 1136 intermesh with or engage the valleys 108 on incremental stretching roller 1134. As the nonwoven precursor web 25 having weakened, melt-stabilized locations 1202 passes through the incremental stretching system 1132, the nonwoven precursor web 25 is subjected to tensioning in the CD direction causing the nonwoven precursor web 25 to be extended in the CD direction. Alternatively, or additionally, the nonwoven precursor web 25 may be tensioned in the MD. The tensioning force placed on the nonwoven precursor web 25 can be adjusted such that it causes the weakened, melt-stabilized locations 1202 to rupture creating a plurality of formed SAN apertures 1204 (SAN standing for Stretch Apertured Nonwoven) coincident with the weakened melt-stabilized locations 1202 in the nonwoven precursor web 25 to form apertured web 1. However, the bonds of the nonwoven precursor web 25 can be strong enough such that they do not rupture during tensioning, thereby maintaining the nonwoven web in a coherent condition even as the weakened, melt-stabilized locations rupture.

As shown in FIG. 14, different portions of incremental stretching rollers 1134 and 1136 can have different depth of valleys 108 and height of ridges 106 about the circumference of incremental stretching roller 1136 and incremental stretching roller 1134. The distance between valleys 108 and ridges 106 and incremental stretching rollers 1134 and 1136 can also be varied. Configuring the rolls in this manner will allow different amounts of stretching to be applied to different portions of the nonwoven precursor web 25, thereby forming an apertured web 1 having portions that differ from one another which can be used for topsheet 20.

Figure 15:
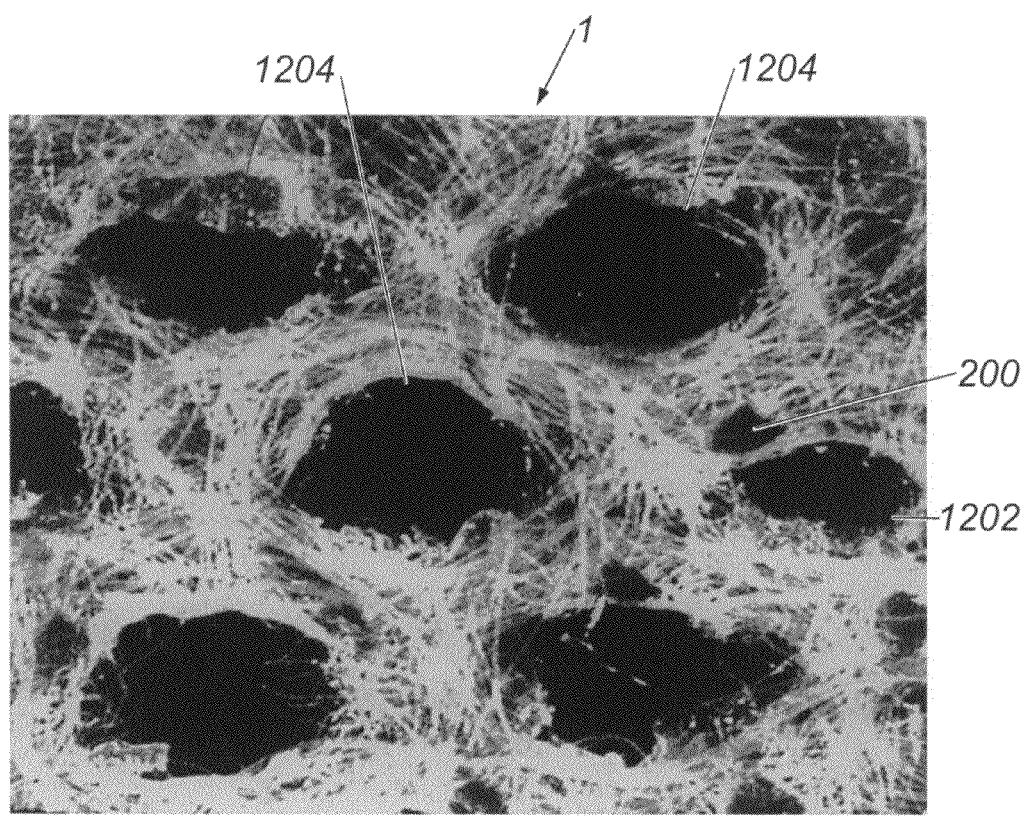
FIG. 15 is an image of a stretch apertured nonwoven.

Referring now to FIG. 15 there is shown an image of the apertured web 1 after the precursor web 25 has been subjected to the tensioning force applied by the incremental stretching system 1132. As can be seen in the image, the apertured web 1 has a plurality of SAN apertures 1204 which are coincident with the weakened, melt-stabilized locations 1202 of the nonwoven precursor web 25, shown in FIG. 13.

Other structures of incremental stretching mechanisms suitable for incrementally stretching or tensioning the nonwoven web are described in International Patent Publication No. WO 95/03765, published Feb. 9, 1995, in the name of Chappell, et al.

The nonwoven apertured web 1 can be taken up on wind-up roll 180 and stored. Alternatively, the nonwoven apertured web 1 may be fed directly to a production line where it is used to form a topsheet on a disposable absorbent article.

Figure 16:
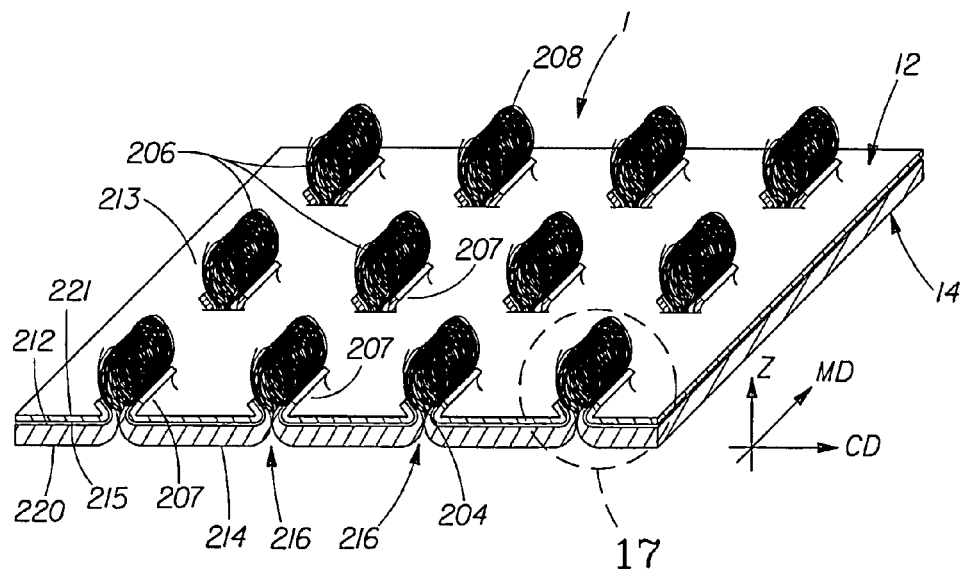
FIG. 16 is a schematic of a web having tufts.

The first portion 60 and/or the second portion 70 can comprise tufts 206. Tufts 206 can comprise a laminate web 1 comprised of two or more layers in which one of the layers is pushed into the other layer or protrudes through apertures in the other layer, an example of which is shown in FIG. 16. The layers are referred to herein as generally planar, two-dimensional precursor webs, such as first precursor web 220 and second precursor web 221. Either precursor web can be a film, a nonwoven, or a woven web. First precursor web 220 and second precursor web 221 (and any additional webs) can be joined with or without adhesive, thermal bonding, ultrasonic bonding and the like. First precursor web 220 and second precursor web 221 can correspond to the upper layer 21 and lower layer 22 of topsheet 20, as shown in FIG. 1.

Web 1 has a first side 12 and a second side 14, the term "sides" being used in the common usage of generally planar two-dimensional webs, such as paper and films that have two sides when in a generally flat condition. First precursor web 220 has a first precursor web first surface 212 and a first precursor web second surface 214. Second precursor web 221 has a second precursor web first surface 213 and a second precursor web second surface 215. Web 1 has an MD and a CD as is commonly known in the art of web manufacture. The first precursor web 220 can be a nonwoven web comprised of substantially randomly oriented fibers, a polymer film, or a woven web. By "substantially randomly oriented" is meant that, due to processing conditions of the precursor web, there may be a higher amount of fibers oriented in the MD than the CD, or vice-versa. Second precursor web 221 can be a nonwoven web similar to the first precursor web 220, or a polymer film or an apertured polymer film, such as a polyethylene film.

Figure 17:
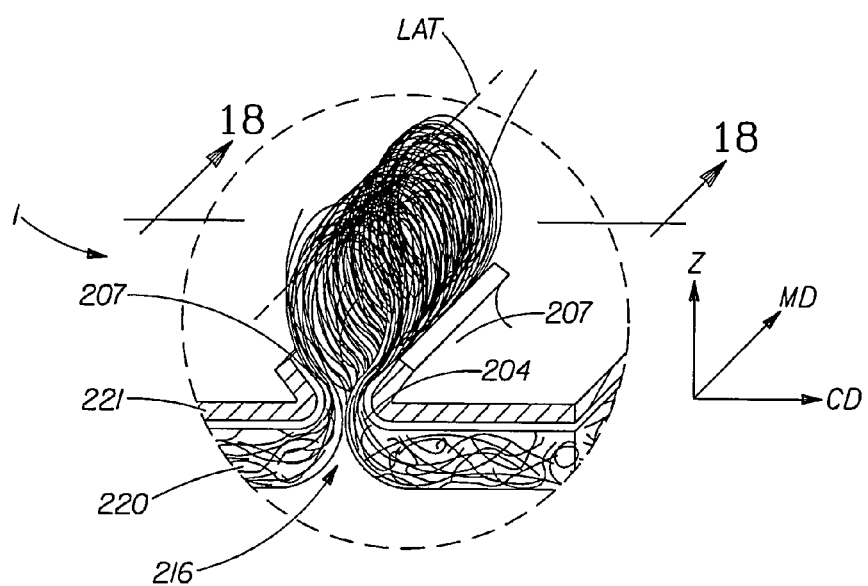
FIG. 17 is a cutaway section of a web having tufts as indicated by Cutaway 17 in FIG. 16.

In one embodiment, first side 12 of web 1 is defined by exposed portions of the second precursor web first surface 213 and one or more discrete tufts 206 which are integral extensions of the fibers of a nonwoven first precursor web 220. Tufts 206 can protrude through apertures in the second precursor web 221. As shown in FIG. 17, each tuft 206 can comprise a plurality of looped fibers 208 extending through second precursor web 221 and outwardly from the second precursor web first surface 213 thereof.

Tufts can be formed by urging fibers out-of-plane in the z-direction at discrete, localized, portions of first precursor web 220.

First precursor web 220 can be a fibrous woven or nonwoven web comprising elastic or elastomeric fibers. Elastic or elastomeric fibers can be stretched at least about 50% and return to within 10% of their original dimension. Tufts 206 can be formed from elastic fibers if the fibers are simply displaced due to the mobility of the fiber within the nonwoven, or if the fibers are stretched beyond their elastic limit and are plastically deformed.

Second precursor web 221 can be virtually any web material, the only requirement being that it have sufficient integrity to be formed into the laminate by the process described below, and that it have elongation properties relative to first precursor web 220, such that upon experiencing the strain of fibers from first precursor web 220 being urged out-of-plane in the direction of second precursor web 221, second precursor web 221 will be urged out of plane (e.g. by stretching) or rupture (e.g. by tearing due to extensional failure). If rupture occurs, IPS apertures 204 can be formed at the rupture locations (IPS stands for Inter-Penetrating SELF (SELF meaning structural elastic like film, see e.g. U.S. Pat. No. 5,518,801). Portions of first precursor web 220 can extend through IPS apertures 204 (i.e., "push through" or protrude through) in second precursor web 221 to form tufts 206 on first side 12 of web 1. In one embodiment second precursor web 221 is a polymer film. Second precursor web 221 can also be a woven textile web, a nonwoven web, a polymer film, an apertured polymer film, a paper web, (e.g., tissue paper), a metal foil (e.g., aluminum wrapping foil), a foam (e.g., urethane foam sheeting), or the like.

As shown in FIGS. 16 and 17, tufts 206 can extend through IPS apertures 204 in second precursor web 221. IPS apertures 204 can be formed by locally rupturing second precursor web 221. Rupture may involve a simple splitting open of second precursor web 221, such that IPS apertures 204 are in-plane (MD-CD) two-dimensional apertures. However, for some materials, such as polymer films, portions of second precursor web 221 can be deflected or urged out-of-plane (i.e., the plane of second precursor web 221) to form flap-like structures, referred to herein as a flap, or flaps, 207. The form and structure of flaps 207 can be dependent upon the material properties of second precursor web 221. Flaps 207 can have the general structure of one or more flaps, as shown in FIGS. 16 and 17. In other embodiments, flap 207 can have a more volcano shaped structure, as if the tuft 206 is erupting from the flap 207.

Tufts 206 can be, in a sense, "pushed through" (or protrude through) second precursor web 221 and can be "locked" in place by frictional engagement with IPS apertures 204. This indicates a certain amount of recovery at the opening that tends to constrain tuft 206 from pulling back out through IPS apertures 204. The frictional engagement of the tufts and openings can provide for a laminate web structure having tufting on one side that can be formed without adhesives or thermal bonding.

Tufts 206 can be spaced sufficiently closely so as to effectively cover first side 12 of web 1 when tufts 206 protrude through second precursor web 221. In such an embodiment, both sides of web 1 appear to be nonwoven, with a difference between first side 12 and second side 14 being a difference in surface texture. Therefore, in one embodiment, the web 1 can be described as a laminate material of two or more precursor webs, wherein both sides of the laminate web are substantially covered by fibers from only one of the precursor webs.

The looped fibers 208 can be substantially aligned such that tuft 206 has a distinct linear orientation and a tuft long axis LAT, as shown in FIG. 17. Tufts 206 can also have a short axis TS generally orthogonal to tuft long axis LAT in the MD-CD plane. In the embodiment shown in FIGS. 17 and 18, tuft long axis LAT is parallel to the MD. The tuft 206 can have a symmetrical shape in the MD-CD plane, such as a circular shape or square shape. Tufts 206 can have an aspect ratio (ratio of longest dimension to shortest dimension, both measured in the MD-CD plane) greater than 1. In one embodiment, all the spaced apart tufts 206 have generally parallel tuft long axis LAT. The number of tufts 206 per unit area of web 1, i.e., the area density of tufts 206, can be varied from about 1 tuft/cm$^2$ to about 100 tufts/cm$^2$. There can be at least about 10, or at least about 20 tufts/cm$^2$.

Figure 18:
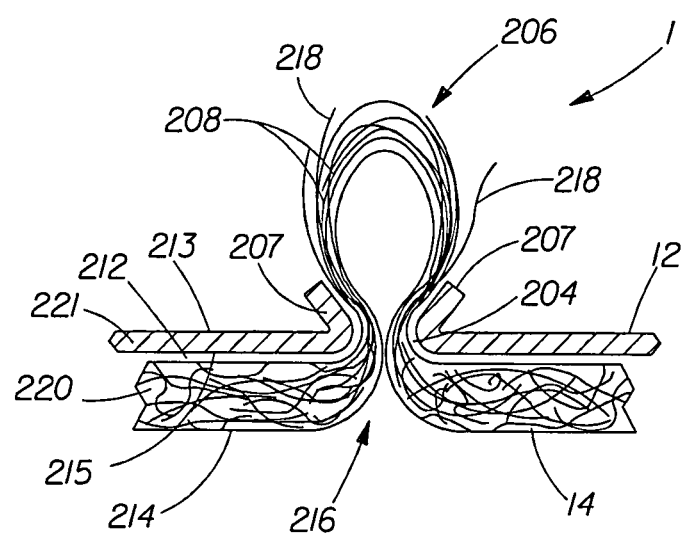
FIG. 18 is a cross section of a web having tufts as indicated by Section 18-18 in FIG. 17.

In another embodiment, each tuft 206 can comprise a plurality of non-looped fibers 218 (as shown in FIG. 18) that extend outwardly from the second precursor web first surface 213. In general, the looped fibers 208 or non-looped fibers 218 of the tufts 206 comprise fibers that are integral with and extend from the fibers of the first precursor web 220.

Figure 19:
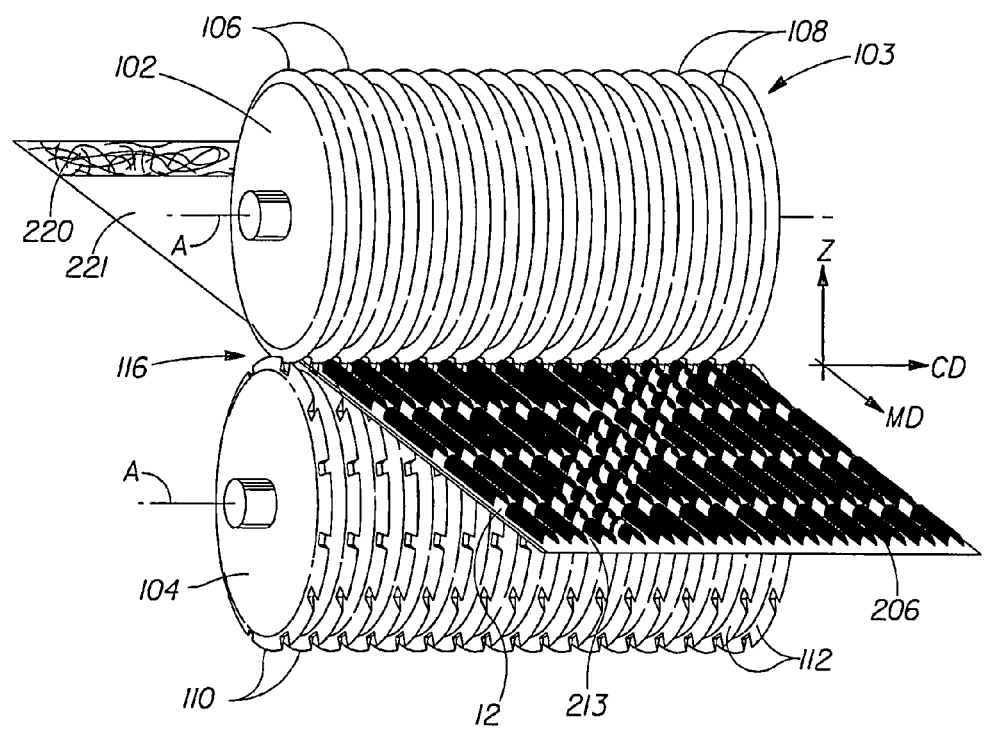
FIG. 19 is a schematic of an apparatus for forming a web having tufts.

Referring to FIG. 19 there is shown an apparatus and method for making a web 1 comprising tufts 206. The forming apparatus 103 comprises a pair of intermeshing rolls 102 and 104, each rotating about an axis A, the axes A being parallel in the same plane. Roll 102 comprises a plurality of ridges 106 and corresponding valleys 108 which can extend unbroken about the entire circumference of roll 102. Roll 104 can comprise a plurality of rows of circumferentially-extending ridges that have been modified to be rows of circumferentially-spaced teeth 110 that extend in spaced relationship about at least a portion of roll 104. Portions of roll 104 can be without teeth 110 to permit forming a web 1 having portions without tufts 206. Size and/or spacing of teeth 110 can be varied, as shown in FIG. 19, to permit formation of a web 1 having different size tufts 206 in different portions and/or have portions without tufts 206.

The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the valleys 108 of roll 102. Both or either of rolls 102 and 104 can be heated by means known in the art such as by using hot oil filled rollers or electrically-heated rollers.

In FIG. 19, the forming apparatus 103 is shown as having one patterned roll, e.g., roll 104, and one non-patterned grooved roll 102. Two patterned rolls 104 having either the same or differing patterns, in the same or different corresponding regions of the respective rolls can be used. Such an apparatus can produce webs having tufts 206 protruding from both sides of the web 1. An apparatus can be designed to have teeth pointing in opposite directions on the same roll. This can result in a web with tufts 206 being produced on both sides of the web.

Web 1 can be made by mechanically deforming precursor webs, such as first precursor web 220 and second precursor web 221, that can each be described as generally planar and two dimensional prior to processing by the apparatus shown in FIG. 19. By "planar" and "two dimensional" is meant simply that the webs start the process in a generally flat condition relative to the web 1 that has distinct, out-of-plane, z-direction three-dimensionality due to the formation of tufts 206. "Planar" and "two-dimensional" are not meant to imply any particular flatness, smoothness or dimensionality.

The process and apparatus for forming tufts 206 is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". As described below, the teeth 110 of roll 104 have a geometry associated with the leading and trailing edges that permit the teeth to essentially "push" through the plane of the first precursor web 220 and second precursor web 221. In a two layer laminate web, the teeth 110 urge fibers from a first precursor web 220 simultaneously out-of-plane and through the plane of second precursor web 221. Therefore, tufts 206 of web 1 can be "tunnel-like" tufts of looped fibers 208 extending through and away from the second precursor web first surface 213 and can be symmetrically shaped.

First precursor web 220 and second precursor web 221 are provided either directly from their respective web making processes or indirectly from supply rolls and moved in the machine direction to the nip 116 of counter-rotating intermeshing rolls 102 and 104. The precursor webs are preferably held in a sufficient web tension so as to enter the nip 116 in a generally flattened condition by means well known in the art of web handling. As first precursor web 220 and second precursor web 221 pass through the nip 116, the teeth 110 of roll 104 which are intermeshed with valleys 108 of roll 102 simultaneously urge portions of first precursor web 220 out of the plane of first precursor web 220, and in some instances, through second precursor web 221 to form tufts 206. In effect, teeth 110 "push" fibers of first precursor web 220 into or through the plane of the second precursor web 221.

As the tip of teeth 110 push into or through first precursor web 220 and second precursor web 221, the portions of the fibers of first precursor web 220 that are oriented predominantly in the CD across teeth 110 are urged by the teeth 110 out of the plane of first precursor web 220. Fibers can be urged out of plane due to fiber mobility, or they can be urged out of plane by being stretched and/or plastically deformed in the z-direction. Portions of first precursor web 220 urged out of plane by teeth 110 push into or through second precursor web 221, which can rupture due to its relatively lower extensibility, thereby resulting in formation of tufts 206 on first side 12 of web 1.

For a given maximum strain (e.g., the strain imposed by teeth 110 of forming apparatus 103), second precursor web 221 can actually fail under the tensile loading produced by the imposed strain. That is, for the tufts 206 to be disposed on the first side 12 of web 1, second precursor web 221 must have sufficiently low fiber mobility (if any) and/or relatively low elongation-to-break such that it locally (i.e., in the area of strain) fails in tension, thereby producing IPS apertures 204 through which tufts 206 can extend.

In one embodiment, second precursor web 221 has an elongation to break in the range of 1%-5%. While the actual required elongation to break depends on the strain to be induced to form web 1, it is recognized that in some embodiments, second precursor web 221 can exhibit a web elongation-to-break of about 6%, about 7%, about 8%, about 9%, about 10%, or more. It is also recognized that actual elongation-to-break can depend on the strain rate, which, for the apparatus shown in FIG. 19, is a function of line speed. Elongation to break of webs can be measured by means known in the art, such as by standard tensile testing methods using standard tensile testing apparatuses, such as those manufactured by Instron, MTS, Thwing-Albert, and the like.

Furthermore, relative to first precursor web 220, second precursor web 221 can have lower fiber mobility (if any) and/or lower elongation-to-break (i.e., elongation-to-break of individual fibers, or, if a film, elongation-to-break of the film) such that, rather than extending out-of-plane to the extent of the tufts 206, second precursor web 221 can fail in tension under the strain produced by the formation of tufts 206, e.g., by the teeth 110 of forming apparatus 103. In one embodiment, second precursor web 221 exhibits sufficiently low elongation-to-break relative to first precursor web 220 such that flaps 207 of IPS apertures 204 only extend slightly out-of-plane, if at all, relative to tufts 206. Second precursor web 221 can have an elongation to break of at least about 10% less than the first precursor web 220, or at least about 30% less, or at least about 50% less, or at least about 100% less than that of first precursor web 220.

Figure 20A:
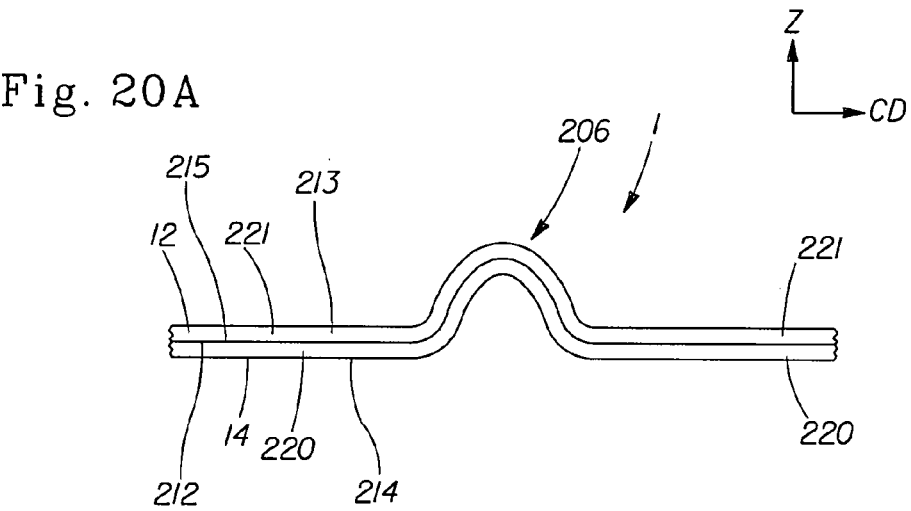
FIG. 20A is a schematic of a tufted web.
Figure 20B:
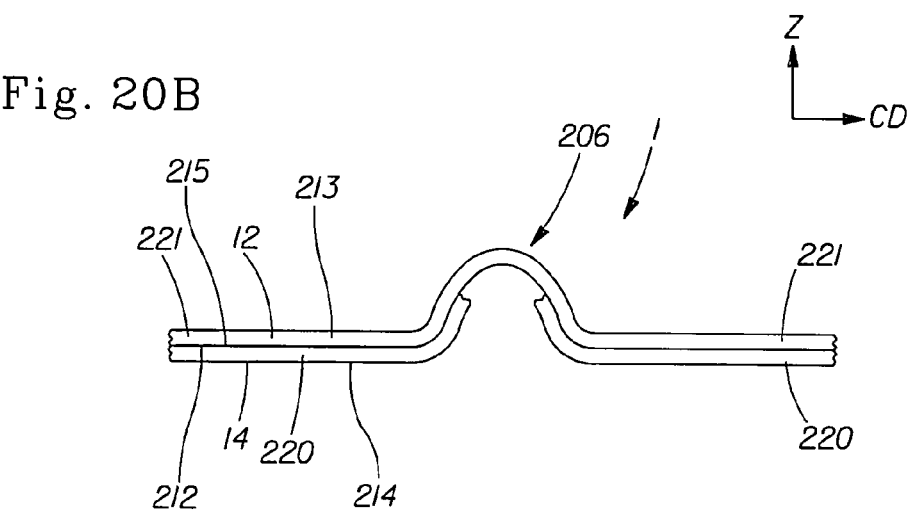
FIG. 20B is schematic of a tufted web.

If second precursor web 221 merely deforms or stretches in the region of induced strain, but does not actually fail, a tuft 206 that does not protrude through second precursor web 221 can be formed, as shown in FIGS. 20A and 20B. Tufts 206 illustrated in FIGS. 20A and 20B are in effect nested in the second precursor web 221. As shown in FIGS. 20A, first precursor web 220 can be pushed into the MD-CD plane of the second precursor web 221 without rupturing second precursor web 221 or tearing first precursor web 220. In essence, first precursor web 220 is indented into second precursor web 221 to form tuft 206. As shown in FIG. 20B, first precursor web 220 can be indented into and nested within second precursor web 221 and first precursor web 220 can be ruptured to form tuft 206.

The number, spacing, and size of tufts 206 can be varied by changing the number, spacing, and size of teeth 110 and making corresponding dimensional changes as necessary to roll 104 and/or roll 102. This variation, together with the variation possible in first precursor web 220 and second precursor web 221 permits many varied webs 1 to be made for many purposes such as personal care items, as disclosed in WO 01/76523. A web 1 comprising a nonwoven/film first precursor web/second precursor web combination can also be used as a component in disposable absorbent articles.

A tufted web 1 can be formed from a nonwoven first precursor web 220 having a basis weight of between about 60 gsm and about 100 gsm (80 gsm being practical) and a polyolefinic film (e.g., polyethylene or polypropylene) second precursor web 221 having a density of about 0.91-0.94 g/cm$^3$ and a basis weight of about 20 gsm.

Figure 21:
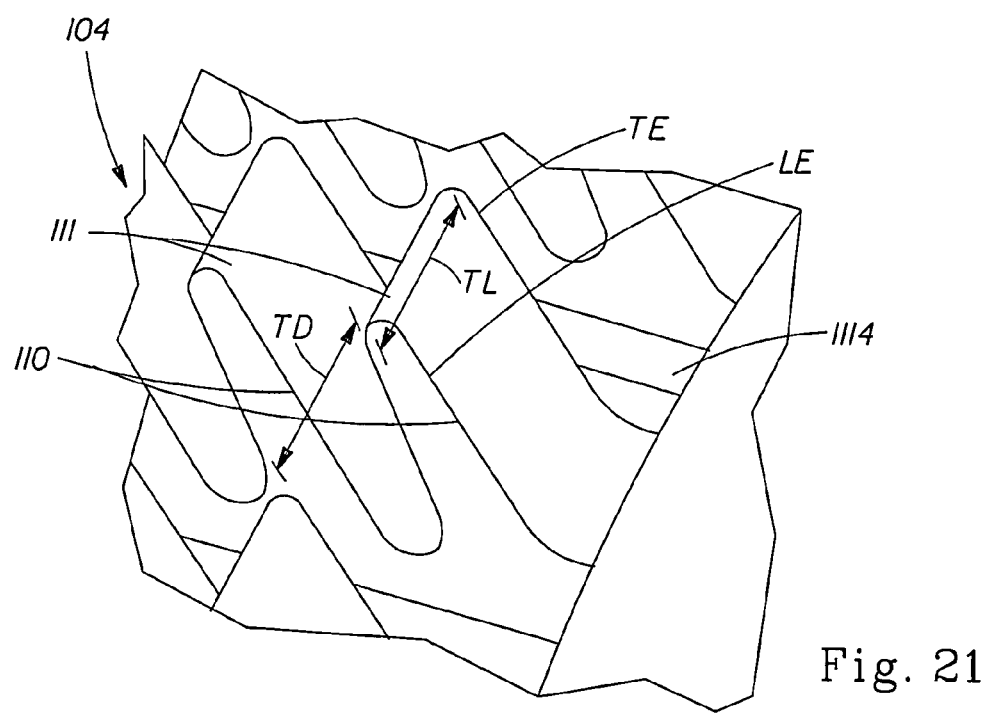
FIG. 21 is a schematic of a roll having teeth.

An enlarged view of teeth 110 is shown in FIG. 21. Teeth 110 can have a circumferential length dimension TL measured generally from the leading edge LE to the trailing edge TE at the tooth tip 111 of about 1.25 mm and can be uniformly spaced from one another circumferentially by a distance TD of about 1.5 mm. For making a web 1 from precursor web 25 having a total basis weight in the range of about 60 to about 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (about 0.040 inches) and about 5 mm (about 0.200 inches). Depth of engagement E can be from about 0.5 mm to about 5 mm (up to a maximum equal to tooth height TH). Of course, E, P, TH, TD and TL can be varied independently of each other to achieve a desired size, spacing, and area density of tufts 206.

The tooth tip 111 can be elongated and can have a generally longitudinal orientation, corresponding to a long axes LA of tufts 206 and discontinuities 216. It is believed that to get the tufted, looped tufts 206 of the web 1 that can be described as being terry cloth-like, the LE and TE should be very nearly orthogonal to the cylindrical surface 1114 of roll 104. As well, the transition from the tip 111 and LE or TE should be a sharp angle, such as a right angle, having a sufficiently small radius of curvature such that teeth 110 can push through second precursor web 221 at the LE and TE. Without being bound by theory, it is believed that having relatively sharply angled tip transitions between the tip of tooth 110 and the LE and TE permits the teeth 110 to push through first precursor web 220 and second precursor web 221 "cleanly", that is, locally and distinctly, so that the first side 12 of the resulting web 1 has tufts 206. When so processed, the web 1 may not be imparted with any particular elasticity, beyond what the first precursor web 220 and second precursor web 221 may have possessed originally. The pushing through of the second precursor web 221 can result in a small portion of the second precursor web 221 forming "confetti" or small pieces.

Web 1 having tufts 206 can be used as a topsheet 20 or a portion of topsheet 20 of absorbent article 10. Web 1 having tufts 206 can be beneficial as a topsheet 20 for absorbent articles due to the combination of excellent fluid acquisition and distribution to the absorbent core 40, and excellent prevention of rewet to the body-facing surface of topsheet 20 when in use. Rewet can be a result of at least two causes: (1) squeezing out of the absorbed fluid due to pressure on the absorbent article 10; and/or (2) wetness entrapped within or on the topsheet 20.

Surface texture in various portions of the topsheet 20 can be created by providing tufts 206. Tufts 206 can be oriented such that tufts 206 comprise a portion of the body facing surface 23 of the topsheet 20. Tufts 206 can be oriented such that tufts 206 are oriented on the garment facing surface of the topsheet 20.

A topsheet 20 can be made by using a nonwoven first precursor web 220 and a fluid impermeable polyethylene film second precursor web 221. The basis weights of the component webs can be varied, however, in general due to cost and benefit considerations a total basis weight of between about 20 gsm and 80 gsm can be desirable for web 1. When made as a film/nonwoven laminate, web 1 combines the softness and fluid capillarity of fiber tufts and the rewet prevention of a fluid impermeable polymer film.

The first portion 60 can comprise tufts 206. The second portion 70 can comprise tufts 206. The first portion 60 and the second portion 70 can both comprise tufts 206, wherein the tufts in the first portion 60 differ in structure from the tufts in the second portion 70. The difference in the tufts 206 can be the size of the tuft in the out-of-plane dimension, z. The difference in the tufts 206 can be the size or shape of the tuft in the MD-CD plane. The size of a tuft is the largest dimension of the tuft in a plane parallel to the MD-CD plane (presented to the viewer of the topsheet). The difference in the tufts 206 can be the form of the tuft 206 with respect to whether or not the tuft 206 protrudes through the second precursor web 221 or is nested within second precursor web 221. The difference in the tufts 206 can be the color of the tufts 206. Different colors of tufts 206 can help the wearer understand that different portions of the absorbent article 10 may perform differently, help her position the absorbent article 10 properly in her panty, and provide for emotional confidence.

In one embodiment, tufts 206 can protrude through the second precursor web 221 and be extending from the body facing side of the topsheet 20. In another embodiment, tufts 206 can be extending from the garment facing side of the topsheet 20.

Figure 22A:
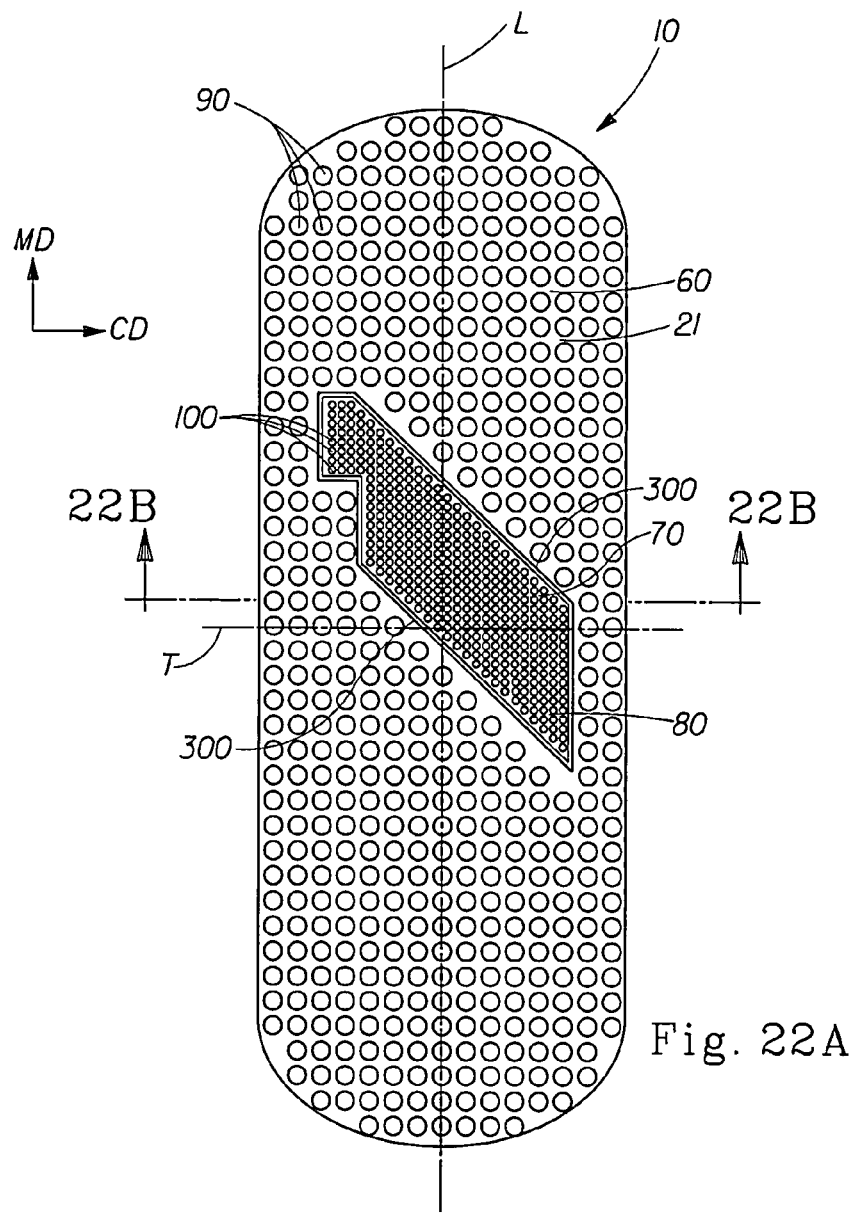
FIG. 22A is an illustration of an absorbent article having a first portion having a boundary defined by a channel.
Figure 22B:
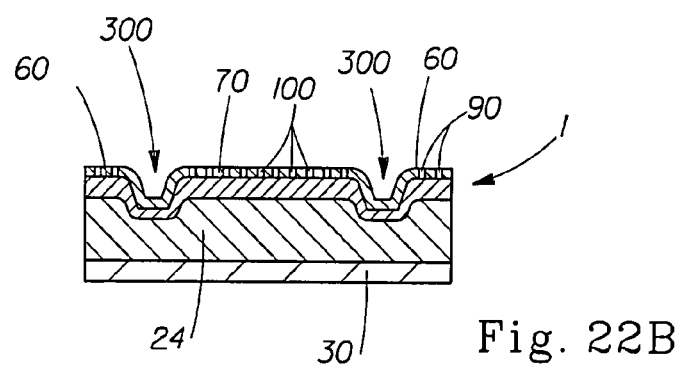
FIG. 22B a cross section as indicated by Section 22B in FIG. 22A.

In one embodiment, as shown in FIG. 22A, the structurally modified zone 80 can have a boundary wherein at least part of the boundary is defined by a channel 300. That is, for a structurally modified zone 80, a channel 300 can surround or partially surround the structurally modified zone 80 and can be contiguous with the particular structurally modified zone 80. Channel 300 can be formed by any means known in the art for creating channels in absorbent articles. Suitable processes include compression molding in which the topsheet 20 and absorbent core 40 are compressed leaving an indentation in the body facing surface of the absorbent article. Without being bound by theory, it is thought that the capillary potential of the portion of the absorbent core 40 near a channel 300 can be higher than the capillary potential of portions of the absorbent core 40 away from the channel 300 and that the higher capillary potential can resist fluid transport beyond the channel 300. Similarly, the first portion 60 can also have a boundary wherein at least part of the boundary is defined by a channel 300. A cross section of FIG. 22A, as marked in FIG. 22A, is shown in FIG. 22B.

Figure 23:
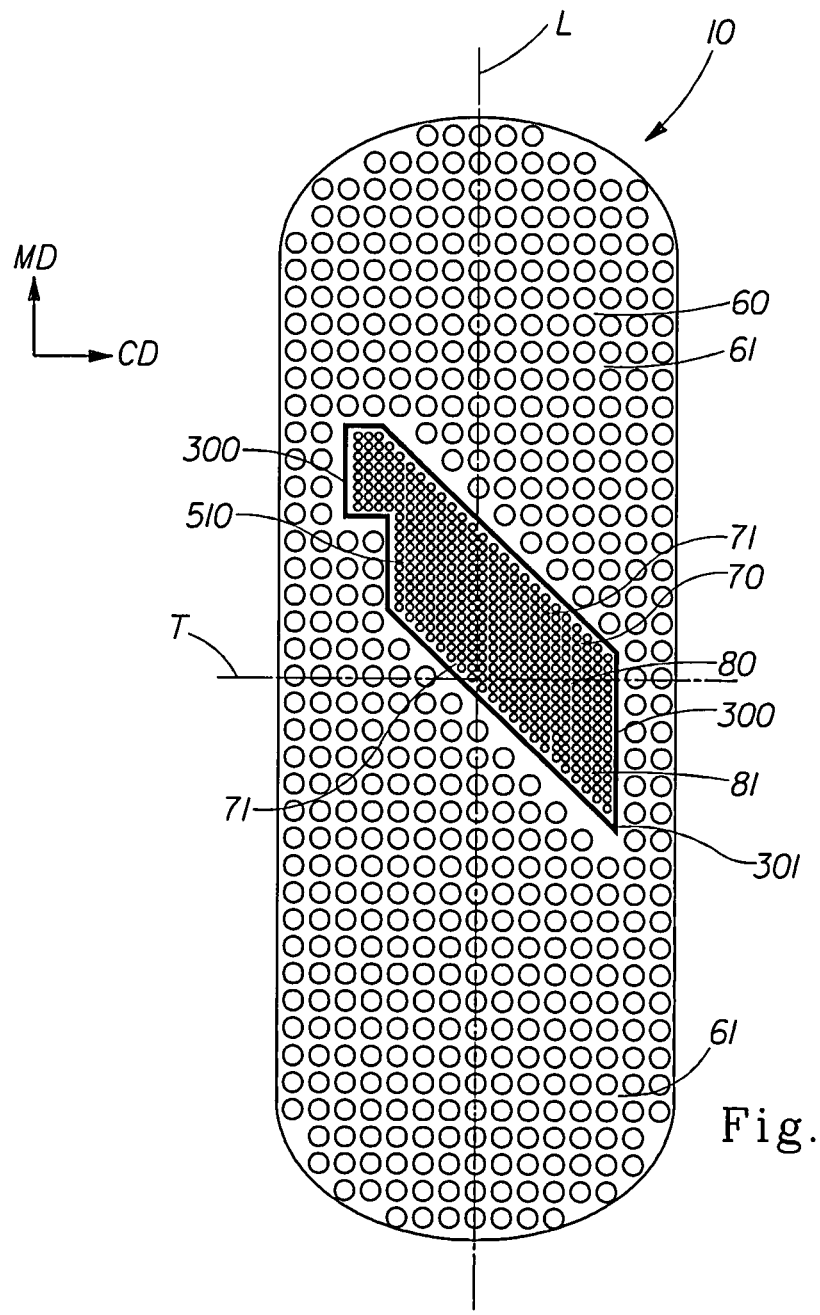
FIG. 23 is an illustration of an absorbent article having a first portion having a first color and a second portion having a second color.

A channel 300 can have at least a portion in which the color differs from the structurally modified zone color 81 of the structurally modified zone 80, as shown in FIG. 23. That is, the channel color 301 of at least a portion of a channel 300 can differ from the structurally modified zone color 81 of the structurally modified zone 80, the boundary of which is defined by the channel 300. A color can be printed or appear on the topsheet 20 or can be printed or appear on a layer underlying the topsheet 20 such that a color is visible through the topsheet 20 when the absorbent article 10 is viewed from the body facing side of the absorbent article 10. The colored portion of channel 300, if present, can have a channel color 301 that varies along the channel. Color can be printed on the topsheet 20 and/or underlying layer or layers by processes known in the art including, but not limited to, ink jet printing, gravure printing, offset printing, and combinations thereof. The constituent material or materials of the colored portions of the topsheet 20 or underlying layers can be colored. The first portion 60 can also have a boundary wherein at least part of the boundary is defined by a channel 300 and at least part of the channel has a channel color 301 that differs from the color of the first portion 60. Colored channels 300 may effectively communicate and highlight that the structurally modified zone 80 may be a zone having enhanced performance and can provide confidence to the wearer that she is wearing a high performance absorbent article 10. Further, colored channels 300 may provide a visual reference mark that helps the wearer evaluate proper wearing time for the absorbent article 10.

As illustrated in FIG. 23, the first portion 60 can have a first color 61 and the second portion 70 can have a second color 71, wherein the first color 61 differs from the second color 71. Without being bound by theory, it is thought that the difference in colors can aid the wearer in properly placing the absorbent article 10 in her panty. The wearer can correlate the relative location of different portions of the absorbent article 10, which can be identified by color, with the staining pattern and make judgments about proper placement and wear time. The difference in colors can also communicate the difference in performance of different portions of the absorbent article 10 and provide the wearer with visual cues regarding wear time, fluid entry, and fluid spreading.

As shown in FIG. 23, the second portion 70 can comprise a lotion 510.

The difference in color can be greater than about 3.5, as characterized by the CIE LAB scale. The difference in color can be greater than about 1.1, as characterized by the CIE LAB scale. The difference in color can be greater than about 6, as characterized by the CIE LAB scale.

Absorbent core 40 can be formed from any of the materials well known to those of ordinary skill in the art. Examples of such materials include multiple plies of creped cellulose wadding, fluffed cellulose fibers, wood pulp fibers also known as airfelt, textile fibers, a blend of fibers, a mass or batt of fibers, airlaid webs of fibers, a web of polymeric fibers, and a blend of polymeric fibers.

In one embodiment absorbent core 40 can be relatively thin, less than about 5 mm in thickness, or less than about 3 mm, or less than about 1 mm in thickness. Thickness can be determined by measuring the thickness at the midpoint along the longitudinal centerline of the pad by any means known in the art for doing while under a uniform pressure of 1.72 kPa. The absorbent core can comprise absorbent gelling materials (AGM), including AGM fibers, as is known in the art.

Backsheet 30 can comprise any of the materials known in the art for backsheets, such as polymer films and film/nonwoven laminates. To provide a degree of softness and vapor permeability for the garment-facing side of absorbent article 10, backsheet 30 can be a vapor permeable outer layer on the garment-facing side of the absorbent article 10. The backsheet 30 can be formed from any vapor permeable material known in the art. Backsheet 30 can comprise a microporous film, an apertured formed film, or other polymer film that is vapor permeable, or rendered to be vapor permeable, as is known in the art. One suitable material is a soft, smooth, compliant, vapor pervious material, such as a nonwoven web that is hydrophobic or rendered hydrophobic to be substantially liquid impermeable.

Other materials and components of absorbent articles 10 are contemplated to be within the scope of the description, including those disclosed in U.S. Pat. No. 4,950,264 issued to Osborn III Aug. 21, 1990 and U.S. Pat. No. 5,439,458 issued to Noel et al. Aug. 8, 1995.

Components of the absorbent article 10 can be joined by any means known in the art, such as by adhesive bonding, thermal bonding, ultrasonic bonding, and the like. An adhesive can be applied by means known in the art for laying a uniform layer of adhesive, such as by spraying or slot coating. The adhesive can be a fluid permeable adhesive, such as the aforementioned Findley HX1500-1 adhesive.

Figure 24:
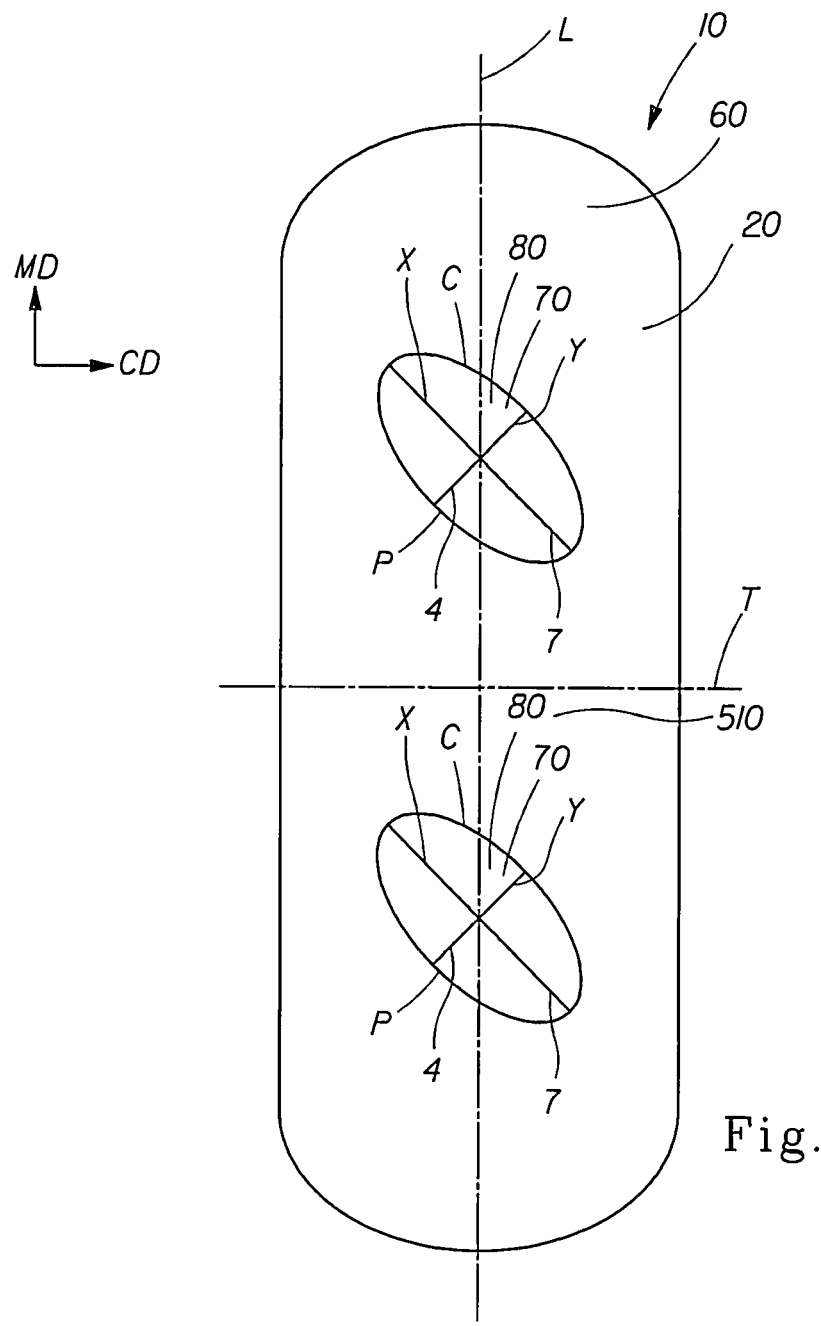
FIG. 24 is an illustration of an absorbent article having two structurally modified zones.

As illustrated in FIG. 24, the topsheet 20 the second portion 70 can have two structurally modified zones 80. In one embodiment, one structurally modified zone 80 can be located towards one end of the topsheet 20 and another structurally modified zone 80 can be located at the other end of the topsheet 20, the ends being characterized based on the MD. Each structurally modified zone 80 can be arranged such that the long axis 7 of each structurally modified zone is asymmetric to the longitudinal centerline L and the transverse centerline T.

Figure 25:
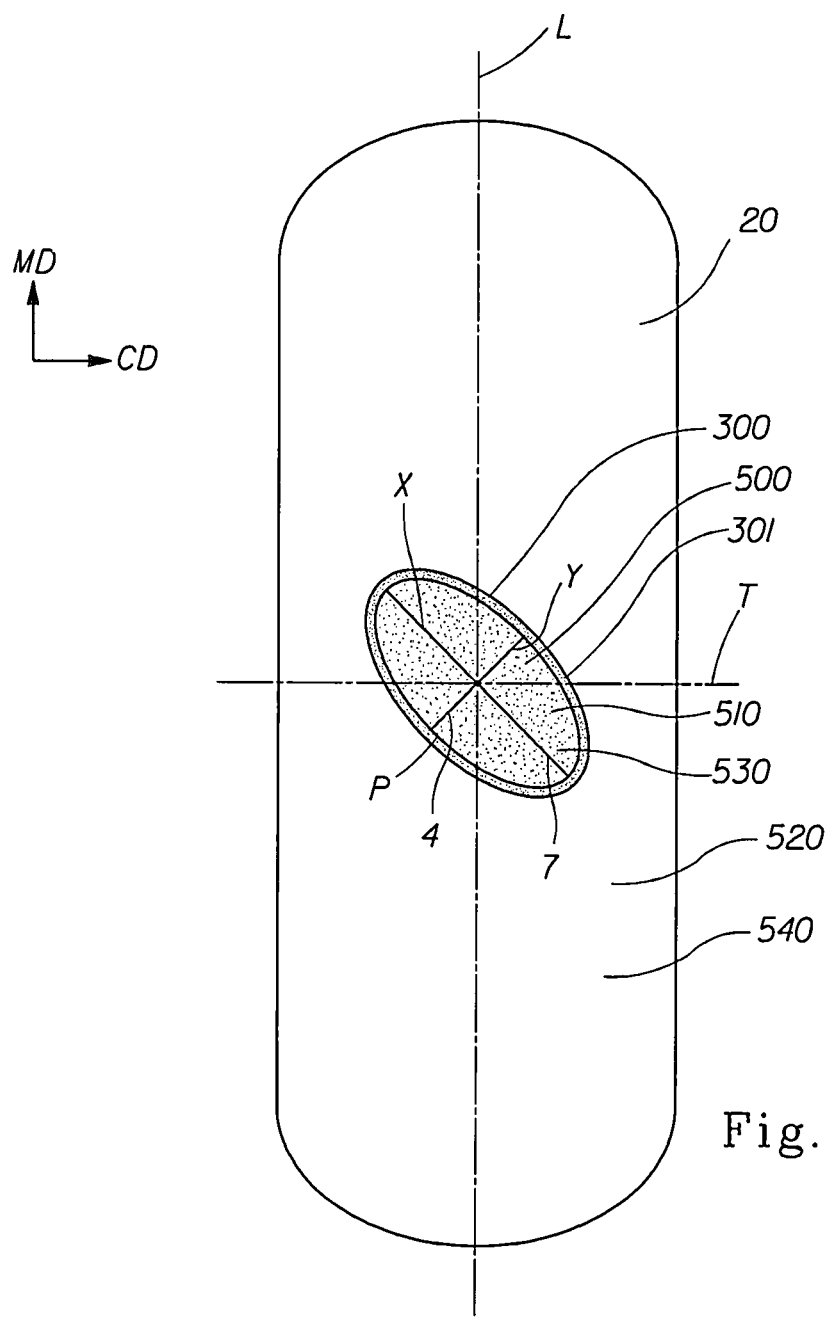
FIG. 25 is an illustration of an absorbent article having a lotion zone.

The absorbent article 10 can comprise a lotion zone 500, as shown in FIG. 25. The lotion zone can have a periphery P, a length X, and a long axis 7. The long axis 7 of the lotion zone 500 can be asymmetric to the longitudinal centerline L and the transverse centerline T. The lotion zone 500 can comprise more than about 5% of the area of the topsheet 20. The lotion zone 500 can comprise more than about 15% of the area of the topsheet 20. The lotion zone 500 can comprise more than about 30% of the area of the topsheet 20. The lotion zone 500 can comprise a lotion 510.

The periphery P of the lotion zone 500 can be arranged such that the periphery P is not symmetric about an axis parallel to the longitudinal centerline L. The long axis 7 of the lotion zone 500 can be asymmetric to the longitudinal centerline L and the transverse centerline T.

The lotion zone 500 can have a width Y and a short axis 4. The lotion zone 500 can be symmetric about the long axis 7 but does not have to be symmetric. The long axis 7 of the lotion zone 500 can be more than about 15 degrees out of symmetry with the longitudinal centerline L. The long axis 7 of the lotion zone 500 can be more than about thirty degrees out of symmetry with the longitudinal centerline L.

Without being bound by theory, it is thought that an asymmetric lotion zone 500 can provide for improved skin care for the wearer of the absorbent article 10 and can improve fluid acquisition by the absorbent article 10. An asymmetric lotion zone 500 can improve the possibilities that the lotion zone will be associated with the wearer's body in the proper location, given that the wearer's body is generally symmetric about the sagittal plane. That is, a lotion zone 500 that is asymmetric with respect to the symmetric portions of the wearer's body may have improved possibilities of being in the right position as the absorbent article 10 moves with respect to the wearer's body. For instance, if the lotion zone 500 is designed to aid in fluid acquisition, an asymmetric lotion zone 500 may improve the probability that as the absorbent article 10 moves relative to the fluid source of the wearer, the lotion zone 500 will be located properly. Fluid sources can be the vagina or urethra in females, the penis in males, and the anus for both males and females.

The lotion 510 can comprise multiple components, as is known in the art. For example, the lotion 510 can comprise an emollient, an immobilizing agent, an optional hydrophilic surfactant, and other components. The emollient can be petrolatum or other material for softening, soothing, coating, lubricating, moisturizing, and/or cleaning the skin. Typical emollients have either a plastic or fluid consistency at 20° C. An immobilizing agent can counteract the tendency of the emollient to migrate from the surface of the topsheet 20. Hydrophilic surfactants can be used to promote rapid transfer of liquids through the topsheet 20. Other components, including perfumes, scents, and pharmacological agents can be employed in the lotion 510.

The lotion 510 can be applied in an effective amount for providing for skin care, skin comfort, and fluid acquisition. The lotion 510 can be applied in an amount between about 0.01 mg/cm$^2$ to about 4 mg/cm$^2$.

As shown in FIG. 25, the topsheet can comprise an edge zone 520. The lotion zone 500 can have a lotion zone color 530 and the edge zone 520 can have an edge zone color 540. The lotion zone color 530 can differ from the edge zone color 540. The difference in color can be greater than about 3.5, as characterized by the CIE LAB scale. The difference in color can be greater than about 1.1, as characterized by the CE LAB scale. The difference in color can be greater than about 6, as characterized by the CIE LAB scale.

Lotion 510 can be applied to the topsheet using approaches known in the art. For example, lotion 510 can be applied by spraying, gravure coating and extrusion coating methods.

Part of a boundary of the lotion zone 500 can be defined by a channel 300. The channel 300 can have a channel color 301. The lotion zone color 530 can differ from at least a portion of the channel 300 having a channel color 301.

Examples of lotions can be found in U.S. Pat. No. 5,968,025 issued to Roe et al. and U.S. Pat. No. 6,627,787 issued to Roe et al., and U.S. Pat. No. 6,825,393 issued to Roe et al.

EXAMPLE

FIG. 22A and FIG. 22B illustrate an example of a topsheet 20 that has a first portion 60 and a second portion 70. The second portion 70 of the topsheet 20 can comprise a structurally modified zone 80. The first apertures 90 can be formed by a portion of roll 104, shown in FIG. 7, that is 100 pitch. Second apertures 100 in the second portion 70 can be formed by a portion of roll 104, shown in FIG. 7, that is 50 pitch. The structurally modified zone 80 can be bound by a channel 300 that has a width ranging from about 1.5 mm to about 4.2 mm.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An absorbent article comprising a topsheet, a backsheet, and an absorbent core disposed between said topsheet and said backsheet, said topsheet comprising a first portion and a second portion, said topsheet having a longitudinal centerline that is coincident with a longitudinal axis of said absorbent article and a transverse centerline, said topsheet having an area;
   wherein said first portion comprises a first structurally modified zone comprising a first plurality of apertures;
   wherein said second portion comprises a second structurally modified zone comprising a second plurality of apertures that are different from said first plurality of apertures, wherein said second structurally modified zone has a periphery, a length, and a long axis, said length being a maximum straight-line dimension between two points on said periphery, said long axis extending between two points on said periphery separated by said length;
   wherein said periphery is not symmetric about an axis parallel to said longitudinal centerline;
   wherein said long axis of said second structurally modified zone is asymmetric to said longitudinal centerline;
   wherein said first plurality of apertures are substantially flat in the plane of said topsheet and wherein at least some of said second plurality of apertures comprises an aperture sidewall that protrudes outwardly from said topsheet in a direction away from said absorbent core; and
   wherein said second structurally modified zone comprises more than about 5% of said area of said topsheet.

2. An absorbent article comprising a topsheet, a backsheet, and an absorbent core disposed between said topsheet and said backsheet, said topsheet comprising:
   a first portion comprising a first plurality of apertures, at least some of which comprising an aperture sidewall that protrudes outwardly from a MD-CD plane of said topsheet in a direction away from said absorbent core;
   a second portion comprising a second plurality of apertures, at least some which being substantially flat wherein an aperture sidewall does not extend substantially beyond said MD-CD plane of said topsheet; and
   an embossed channel disposed between said first portion and said second portion,
   wherein said topsheet comprises a nonwoven.

3. The absorbent article of claim 2, wherein said topsheet is a laminate comprising a film layer and a nonwoven layer.

4. The absorbent article of claim 2, wherein said topsheet is a laminate comprising a first nonwoven layer and a second nonwoven layer.

5. The absorbent article of claim 2, wherein said absorbent article further comprises one or more colors visible through said topsheet, said one or more colors includes a first color associated with said embossed channel and a second color associated with said second portion.

6. The absorbent article of claim 5, wherein said one or more colors includes a third color associated with said first portion.

7. An absorbent article comprising a topsheet, a backsheet, and an absorbent core disposed between said topsheet and said backsheet, said topsheet comprising:
   a first portion comprising a first plurality of apertures, at least some of which comprising an aperture sidewall that protrudes outwardly from a MD-CD plane of said topsheet in a direction away from said absorbent core;
   a second portion comprising a second plurality of apertures, at least some which being substantially flat wherein an aperture sidewall does not extend substantially beyond said MD-CD plane of said topsheet; and
   one or more colors visible through said topsheet, wherein said one or more colors includes a first color associated with said first portion and a second color associated with said second portion,
   wherein said topsheet comprises a nonwoven.

8. The absorbent article of claim 7, wherein said absorbent article further comprises an embossed channel disposed between said first portion and said second portion.

9. The absorbent article of claim 7, wherein said topsheet is a laminate comprising a film layer and a nonwoven layer.

10. The absorbent article of claim 7, wherein said topsheet is a laminate comprising a first nonwoven layer and a second nonwoven layer.

11. An absorbent article comprising a topsheet, a backsheet, and an absorbent core disposed between said topsheet and said backsheet, said topsheet comprising:
    a first portion comprising a first plurality of apertures, at least some of which comprising an aperture sidewall that protrudes outwardly from a MD-CD plane of said topsheet in a direction away from said absorbent core;
    a second portion comprising a second plurality of apertures, at least some which being substantially flat wherein an aperture sidewall does not extend substantially beyond said MD-CD plane of said topsheet;
    an embossed channel disposed between said first portion and said second portion; and
    a plurality of microapertures having an aperture area in said MD-CD plane of less than 0.25 mm$^2$.

12. An absorbent article comprising a topsheet, a backsheet, and an absorbent core disposed between said topsheet and said backsheet, said topsheet comprising:
    a first portion comprising a first plurality of apertures, at least some of which comprising an aperture sidewall that protrudes outwardly from a MD-CD plane of said topsheet in a direction away from said absorbent core;
    a second portion comprising a second plurality of apertures, at least some which being substantially flat wherein an aperture sidewall does not extend substantially beyond said MD-CD plane of said topsheet;

a plurality of microapertures having an aperture area in said MD-CD plane of less than 0.25 mm²; and one or more colors visible through said topsheet, wherein said one or more colors includes a first color associated with said first portion and a second color associated with said second portion.

* * * * *